(12) United States Patent
Tsukagoshi et al.

(10) Patent No.: US 10,939,879 B2
(45) Date of Patent: Mar. 9, 2021

(54) X-RAY CT APPARATUS

(71) Applicant: Toshiba Medical Systems Corporation, Otawara (JP)

(72) Inventors: Shinsuke Tsukagoshi, Nasushiobara (JP); Takahiro Goto, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 227 days.

(21) Appl. No.: 15/659,194

(22) Filed: Jul. 25, 2017

(65) Prior Publication Data
US 2018/0020993 A1 Jan. 25, 2018

(30) Foreign Application Priority Data

Jul. 25, 2016 (JP) .............................. JP2016-145750
Jul. 24, 2017 (JP) .............................. JP2017-142990

(51) Int. Cl.
*A61B 6/03* (2006.01)
*A61B 6/00* (2006.01)

(52) U.S. Cl.
CPC ............... *A61B 6/03* (2013.01); *A61B 6/488* (2013.01); *A61B 6/5205* (2013.01); *A61B 6/4035* (2013.01); *A61B 6/461* (2013.01); *A61B 6/481* (2013.01); *A61B 6/542* (2013.01)

(58) Field of Classification Search
CPC .................................. A61B 6/03; A61B 6/488
See application file for complete search history.

(56) References Cited

U.S. PATENT DOCUMENTS

| 5,386,446 | A | * | 1/1995 | Fujimoto | A61B 6/032 378/15 |
|---|---|---|---|---|---|
| 2006/0262896 | A1 | | 11/2006 | Nishide et al. | |
| 2007/0217567 | A1 | * | 9/2007 | Noshi | A61B 6/504 378/4 |
| 2007/0286332 | A1 | | 12/2007 | Gohno et al. | |
| 2012/0230563 | A1 | * | 9/2012 | Vik | G06T 7/0012 382/128 |
| 2013/0308847 | A1 | * | 11/2013 | Schirra | G06T 11/005 382/131 |
| 2014/0330108 | A1 | * | 11/2014 | Dempsey | A61N 5/1045 600/411 |
| 2016/0310090 | A1 | * | 10/2016 | Klinder | G06T 7/11 |
| 2017/0014069 | A1 | * | 1/2017 | Carmi | A61B 6/4241 |

FOREIGN PATENT DOCUMENTS

| JP | 2006-320523 | 11/2006 |
|---|---|---|
| JP | 4509971 | 7/2010 |
| JP | 5072526 | 11/2012 |

* cited by examiner

*Primary Examiner* — Hugh Maupin
(74) *Attorney, Agent, or Firm* — Oblon, McClelland, Maier & Neustadt, L.L.P.

(57) ABSTRACT

An X-ray CT apparatus according to an embodiment includes setting circuitry. The setting circuitry is configured to set a third plan for a patient, by integrating together a first plan for the patient and a second plan for the patient.

19 Claims, 16 Drawing Sheets

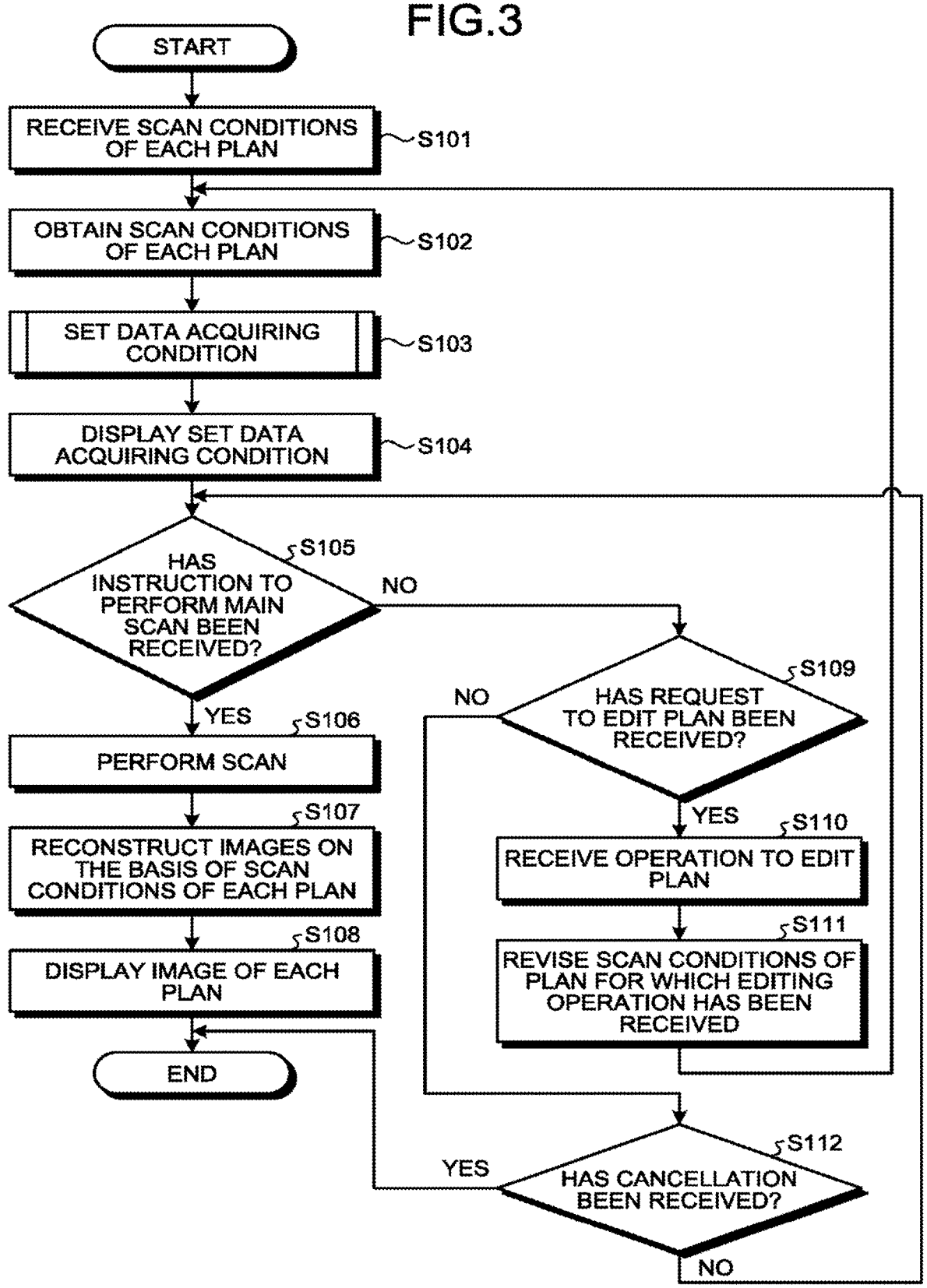

X-RAY CT APPARATUS

CROSS-REFERENCE TO RELATED APPLICATIONS

This application is based upon and claims the benefit of priority from Japanese Patent Application No. 2016-145750, filed on Jul. 25, 2016, and Japanese Patent Application No. 2017-142990, filed on Jul. 24, 2017; the entire contents of which are incorporated herein by reference.

FIELD

Embodiments described herein relate generally to an X-ray Computed Tomography (CT) apparatus.

BACKGROUND

Conventionally, X-ray CT apparatuses have been used in lung cancer examinations performed on the chest. When a medical examination is performed on a patient from whom a lesion site has been detected in a medical examination performed in the past, the imaging process may be performed multiple times depending on the lesion site. For example, an X-ray CT apparatus takes an image of the entire chest and subsequently takes an image of the lesion site.

BRIEF DESCRIPTION OF THE DRAWINGS

FIG. 3 is a flowchart illustrating a processing procedure performed by the X-ray CT apparatus according to the first embodiment;

DETAILED DESCRIPTION

Exemplary embodiments of an X-ray CT apparatus will be explained below, with reference to the accompanying drawings. Possible embodiments are not limited to the embodiments described below. Further, in principle, the explanation of each of the embodiments is similarly applicable to any other embodiments.

An X-ray CT apparatus according to an embodiment includes setting circuitry. The setting circuitry is configured to set a third plan for a patient, by integrating together a first plan for the patient and a second plan for the patient.

First Embodiment

Figure 1:
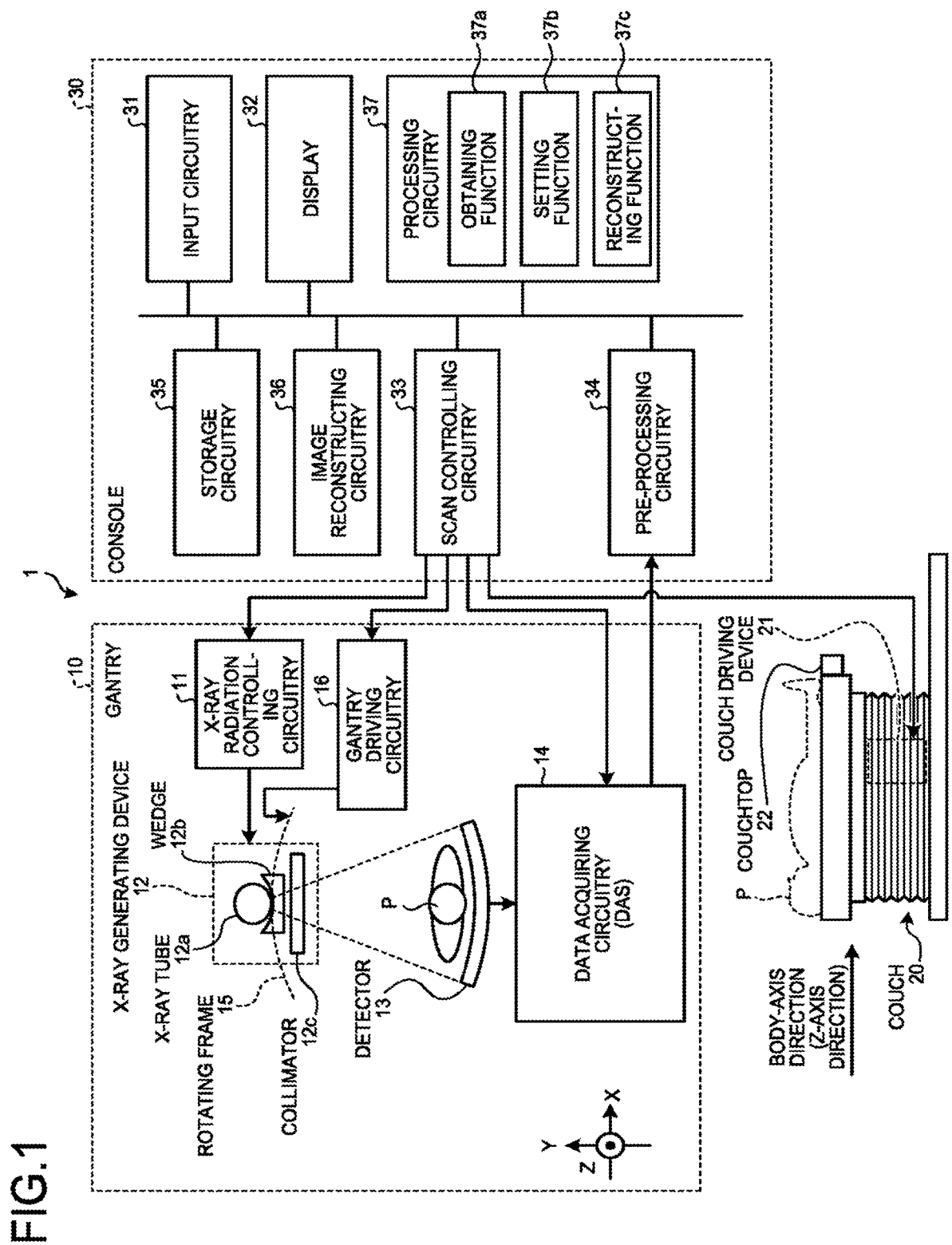
FIG. 1 is a diagram illustrating an exemplary configuration of an X-ray CT apparatus 1 according to a first embodiment.

FIG. 1 is a diagram illustrating an exemplary configuration of an X-ray CT apparatus 1 according to a first embodiment. As illustrated in FIG. 1, the X-ray CT apparatus 1 according to the first embodiment includes a gantry 10, a couch 20, and a console 30.

The gantry 10 is an apparatus configured to radiate X-rays onto an examined subject (hereinafter, "patient") P, to detect X-rays that have passed through the patient P, and to output information to the console 30. The gantry 10 includes X-ray radiation controlling circuitry 11, an X-ray generating device 12, a detector 13, data acquiring circuitry (a Data Acquisition System [DAS]) 14, a rotating frame 15, and gantry driving circuitry 16. Further, as illustrated in FIG. 1, the gantry 10 defines a Cartesian coordinate system based on X-, Y-, and Z-, axes. In other words, the X-axis expresses the horizontal direction, while the Y-axis expresses the vertical direction, and the Z-axis expresses the direction along the rotation center axis of the rotating frame 15 when the gantry 10 is in a non-tilted state.

The rotating frame 15 is an annular frame configured to support the X-ray generating device 12 and the detector 13 so as to oppose each other while the patient P is interposed therebetween and configured to be rotated by the gantry driving circuitry 16 (explained later) at a high speed on a circular orbit centered on the patient P.

The X-ray radiation controlling circuitry 11 is a device configured, as a high-voltage generating unit, to supply a high voltage to an X-ray tube 12a. The X-ray tube 12a is configured to generate X-rays by using the high voltage supplied thereto from the X-ray radiation controlling circuitry 11. The X-ray radiation controlling circuitry 11 is configured to adjust the X-ray dose radiated onto the patient P, by adjusting the X-ray tube voltage and/or the X-ray tube current, supplied to the X-ray tube 12a, under control of scan controlling circuitry 33 (explained later).

Further, the X-ray radiation controlling circuitry 11 is configured, to perform a switching process on a wedge 12b. Further, by adjusting the opening degree of a collimator 12c, the X-ray radiation controlling circuitry 11 is configured to adjust the radiation range (a fan angle or a cone angle) of the X-rays. In the present embodiments, an arrangement is acceptable in which an operator manually switches among a plurality of types of wedges.

The X-ray generating device 12 is a device configured to generate the X-rays and to radiate the generated X-rays onto the patient P. The X-ray generating device 12 includes the X-ray tube 12a, the wedge 12b, and the collimator 12c.

The X-ray tube 12a is a vacuum tube configured to radiate an X-ray beam onto the patient P by using the high voltage supplied thereto by the high-voltage generating unit (not illustrated). The X-ray tube 12a radiates the X-ray beam onto the patient P, as the rotating frame 15 rotates. The X-ray tube 12a is configured to generate the X-ray beam that spreads with the fan angle or the cone angle. For example, under the control of the X-ray radiation controlling circuitry 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is a slit configured to narrow down the radiation range of the X-rays of which the X-ray dose has been adjusted by the wedge 12b, under the control of the X-ray radiation controlling circuitry 11 (explained later).

The gantry driving circuitry 16 is configured to cause the X-ray generating device 12 and the detector 13 to revolve on the circular orbit centered on the patient P, by driving the rotating frame 15 to rotate.

The detector 13 is a two-dimensional array detector (a planar detector) configured to detect the X-rays that have passed through the patient P. In the detector 13, a plurality of rows of detecting elements are arranged along the body-axis direction of the patient P (i.e., the Z-axis direction in FIG. 1), while each row contains a plurality of X-ray detecting elements corresponding to a plurality of channels. More specifically, the detector 13 according to the first embodiment includes the X-ray detecting elements that are arranged in a large number of rows (e.g., 320 rows) along the body-axis direction of the patient P. For example, the detector 13 is capable of detecting X-rays that have passed through the patient P in a wide range such as a range including the lungs or the heart of the patient P.

In the detector 13, for the purpose of making it possible to reconstruct high precision images, the detecting elements are arranged with a pixel pitch (0.25 mm) that is half as large as a conventional pixel pitch. For example, conventional detecting elements are arranged in 80 rows corresponding to 896 channels. In contrast, in the detector 13, the detecting elements are arranged in 160 rows corresponding to 1792 channels. In other words, the detector 13 has a high precision resolution.

The data acquiring circuitry 14 is configured with the DAS and is configured to acquire projection data from X-ray detection data detected by the X-ray detector 13. For example, the data acquiring circuitry 14 generates the projection data by performing an amplifying process, an Analog/Digital (A/D) converting process, a sensitivity correcting process among the channels, and/or the like on X-ray intensity distribution data detected by the detector 13 and further transmits the generated projection data to the console 30 (explained later). For example, when X-rays are continuously emitted from the X-ray tube 12a while the rotating frame 15 is rotating, the data acquiring circuitry 14 acquires a group of projection data corresponding to the entire surrounding (corresponding to 360 degrees). Further, the data acquiring circuitry 14 transmits the acquired pieces of projection data to the console 30 (explained later), while keeping the pieces of projection data in correspondence with the X-ray tubs positions. The X-ray tube positions serve as information indicating projection directions of the pieces of projection, data. Alternatively, the sensitivity correcting process among the channels may be performed by pre-processing circuitry 34 (explained later).

The couch 20 is a device on which the patient P is placed and includes a couch driving device 21 and a couchtop 22, as illustrated in FIG. 1. The couch driving device 21 is configured to move the patient P into the rotating frame 15 by moving the couchtop 22 in the Z-axis direction. The couch driving device 21 is also capable of moving the couchtop 22 in the X-axis direction. The couchtop 22 is a board on which the patient P is placed.

Further, for example, the gantry 10 performs a helical scan by which the patient P is helically scanned by causing the rotating frame 15 to rotate while the couchtop 22 is being moved. In another example, the gantry 10 performs a conventional scan by which the patient P is scanned on a circular orbit by causing the rotating frame 15 to rotate, while the position of the patient P is being fixed after the couchtop 22 is moved. In yet another example, the gantry 10 implements a step-and-shoot method by which the conventional scan is performed in multiple scan areas, by moving the position of the couchtop 22 at regular intervals.

The console 30 is a device configured to receive operations performed by the operator on the X-ray CT apparatus 1 and also configured to reconstruct X-ray CT image data by using the projection data acquired by the gantry 10. As illustrated in FIG. 1, the console 30 includes input circuitry 31, a display 32, the scan controlling circuitry 33, the pre-processing circuitry 34, storage circuitry 35, image reconstructing circuitry 36, and processing circuitry 37.

The input circuitry 31 includes a mouse, a keyboard, a trackball, a switch, a button, a joystick, and/or the like used by the operator of the X-ray CT apparatus 1 to input various types of instructions and various types of settings. The input circuitry 31 is configured to transfer information about the instructions and the settings received from the operator to the processing circuitry 37. For example, the input circuitry 31 receives, from the operator, an image taking condition for the X-ray CT image data, a reconstruction condition used when the X-ray CT image data is reconstructed, an image processing condition applied to the X-ray CT image data, and the like. Further, the input circuitry 31 also receives an operation to select a medical examination to be performed on the patient P. In addition, the input circuitry 31 receives a designation operation to designate a site in an image.

The display 32 is a monitor referenced by the operator and is configured to display the image data generated from the X-ray CT image data for the operator and to display a Graphical User Interface (GUI) used for receiving the various types of instructions and the various types of settings from the operator via the input circuitry 31, under control of the processing circuitry 37. Further, the display 32 is also configured to display a planning screen for a scan plan and a screen of images during a scan. Further, the display 32 is configured to display a virtual patient image, image data, or the like including X-ray exposure information. The virtual patient image displayed by the display 32 will be explained in detail later.

Under the control of the processing circuitry 37, the scan controlling circuitry 33 is configured to control the projection data acquiring process performed by the gantry 10, try controlling operations of the X-ray radiation controlling circuitry 11, the gantry driving circuitry 16, the data acquiring circuitry 14, and the couch driving device 21. More specifically, the scan controlling circuitry 33 is configured to control projection data acquiring processes during an image taking process to acquire a position determining image (a scanogram image) and during a main image taking process (a scan) to acquire an image used for a diagnosis purpose. In the present example, the X-ray CT apparatus 1 according to the first embodiment is configured so as to be able to take a two-dimensional scanogram image and a three-dimensional scanogram image.

For example, by continuously taking images while moving the couchtop 22 at a constant speed and having the X-ray tube 12a fixed in the position corresponding to 0 degrees (a straight-on position of the patient P), the scan controlling circuitry 33 takes the two-dimensional scanogram image. Alternatively, by intermittently moving the couchtop 22 while the X-ray tube 12a is fixed in the position corresponding to 0 degrees, the scan controlling circuitry 33 may take the two-dimensional scanogram image by repeatedly taking images intermittently in synchronization with the moving of the couchtop. In the present example, the scan controlling circuitry 33 is capable of taking the position determining image, not only from the straight-on direction of the patient P, but also from any arbitrary direction (e.g., a lateral direction).

Further, by acquiring the projection data corresponding to the entire surrounding of the patient P during a scanogram image taking process, the scan controlling circuitry 33 takes the three-dimensional scanogram image. For example, the scan controlling circuitry 33 acquires the projection data corresponding to the entire surrounding of the patient P, by performing either a helical scan or a non-helical scan. In this situation, the scan controlling circuitry 33 performs the helical scan or the non-helical scan on a wide range such as the entire chest, the entire abdomen, the entire upper body, or the entire body of the patient P, by using a radiation dose lower than that used in the main image taking process. To perform the non-helical scan, for example, a scan is performed by implementing the step-and-shoot method described above.

When the scan controlling circuitry 33 has acquired the projection data corresponding to the entire surrounding of the patient P in this manner, the image reconstructing circuitry 36 (explained later) is able to reconstruct three-dimensional X-ray CT image data (volume data), and it is therefore possible to generate a position determining image from an arbitrary direction, by using the reconstructed volume data. In this situation, whether the position determining image is taken two-dimensionally or three-dimensionally may arbitrarily be set by the operator or may be set in advance in accordance with specifics of the medical examination.

The pre-processing circuitry 34 is configured to generate corrected projection data by performing a logarithmic converting process as well as correcting processes such as an offset correcting process, a sensitivity correcting process, a beam hardening correcting process, and the like, on the projection data generated by the data acquiring circuitry 14. More specifically, the pre-processing circuitry 34 generates pieces of corrected projection data both for the projection data of the position determining image and for the projection data acquired by performing the main image taking process that were generated by the data acquiring circuitry 14 and further stores the pieces of corrected projection data into the storage circuitry 35.

The storage circuitry 35 is configured to store therein the projection data generated by the pre-processing circuitry 34. More specifically, the storage circuitry 35 stores therein the projection data of the position determining image and the projection data for the diagnosis purpose acquired by performing the main image taking process that were generated by the pre-processing circuitry 34. Further, the storage circuitry 35 is configured to store therein image data generated by the image reconstructing circuitry 36 (explained later), the virtual patient image, and the like. Further, the storage circuitry 35 is configured to store therein a processing result obtained by the processing circuitry 37 (explained later), as appropriate. The virtual patient image and the processing result obtained by the processing circuitry 37 will be explained later.

The image reconstructing circuitry 36 is configured to reconstruct the X-ray CT image data by using the projection data stored in the storage circuitry 35. More specifically, the image reconstructing circuitry 36 reconstructs pieces of X-ray CT image data both from the projection data of the position determining image and the projection data of the image for the diagnosis purpose. In this situation, any of various methods can be used as the reconstruction method. For example, a back projection process may be used. Further, examples of the back projection process include a back projection process using a Filtered Back Projection (FBP) method. Alternatively, the image reconstructing circuitry 36 may reconstruct the X-ray CT image data by using a successive approximation method.

Further, the image reconstructing circuitry 36 is configured to generate image data by performing various types of image processing processes on the X-ray CT image data. After that, the image reconstructing circuitry 36 stores the reconstructed X-ray CT image data and the image data generated by performing the various types of image processing processes, into the storage circuitry 35.

The processing circuitry 37 is configured to exercise overall control of the X-ray CT apparatus 1 by controlling operations of the gantry 10, the couch 20, and the console 30. More specifically, the processing circuitry 37 is configured to control a CT scan performed by the gantry 10, by controlling the scan controlling circuitry 33. Also, the processing circuitry 37 is configured to control the image reconstruction process and the image generating process performed by the console 30, by controlling the image reconstructing circuitry 36. Further, the processing circuitry 37 is configured to exercise control so that the display 32 displays any of the various types image data stored in the storage circuitry 35.

Further, as illustrated in FIG. 1, the processing circuitry 37 is configured to execute an obtaining function 37a, a setting function 37b, and a reconstructing function 37c. In this situation, for example, processing functions executed by the constituent elements of the processing circuitry 37 illustrated in FIG. 1, namely the functions such as the obtaining function 37a, the setting function 37b, and the reconstructing function 37c, are recorded in the storage circuitry 35 in the form of computer-executable programs. The processing circuitry 37 is a processor configured to realize the functions corresponding to the computer programs (hereinafter, "programs"), by reading the programs from the storage circuitry 35 and executing the read programs. In other words, the processing circuitry 37 that has read the programs has the functions illustrated within the processing circuitry 37 in FIG. 1. The obtaining function 37a may be referred to as an obtaining unit, while the setting function 37b may be referred to as a setting unit, and the reconstructing function 37c may be referred to as a reconstructing unit.

The exemplary configuration of the X-ray CT apparatus 1 according to the first embodiment has thus been explained. The X-ray CT apparatus 1 according to the first embodiment configured as described above is used in a medical examination performed on a healthy person or a follow-up patient whose lesion site has already been identified and who is subject to regular follow-up medical examinations.

The X-ray CT apparatus 1 may perform a plurality of medical examinations on an examined site. In this regard, an X-ray CT apparatus according to a conventional technique is configured to receive a plan for each of such medical examinations, to perform a scan, and to reconstruct an image for each of the plans. FIGS. 2A to 2D are drawings for explaining the conventional technique.

Figure 2A:
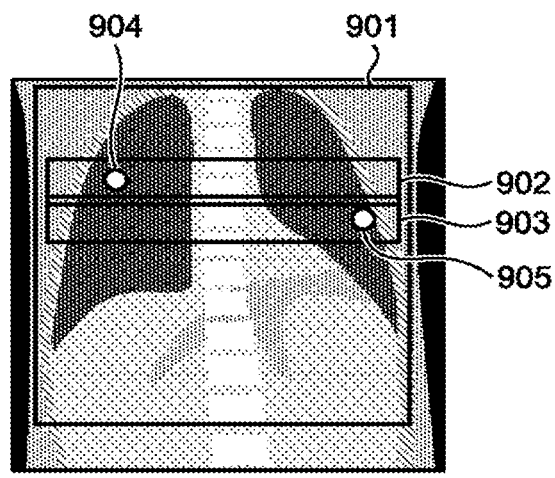
FIG. 2A is a first drawing for explaining a conventional technique.

FIG. 2A illustrates an example of a lung cancer CT medical examination performed on the chest of a follow-up patient from whom a lesion site has been detected in a medical examination performed in the past. FIG. 2A illustrates an example in which the entire chest, a lesion site 904, and a lesion site 905 are imaged. The lesion site 904 and the lesion site 905 are each an example of a region of interest. In that situation, for example, image taking areas are set on the basis of a CT image related to the past medical examination performed on the patient P. More specifically, a region 901 is set as an image taking area for the entire chest, while a region 902 is set as an image taking area including the lesion site 904, and a region 903 is set as an image taking area including the lesion site 905.

Figure 2B:
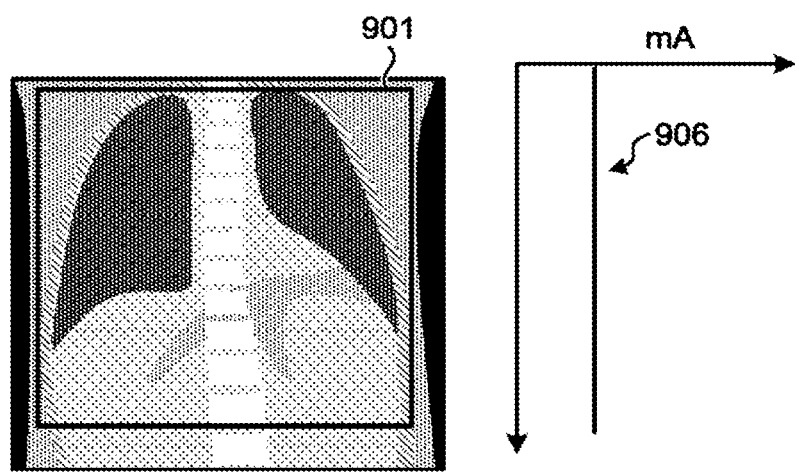
FIG. 2B is a second drawing for explaining the conventional technique.
Figure 2C:
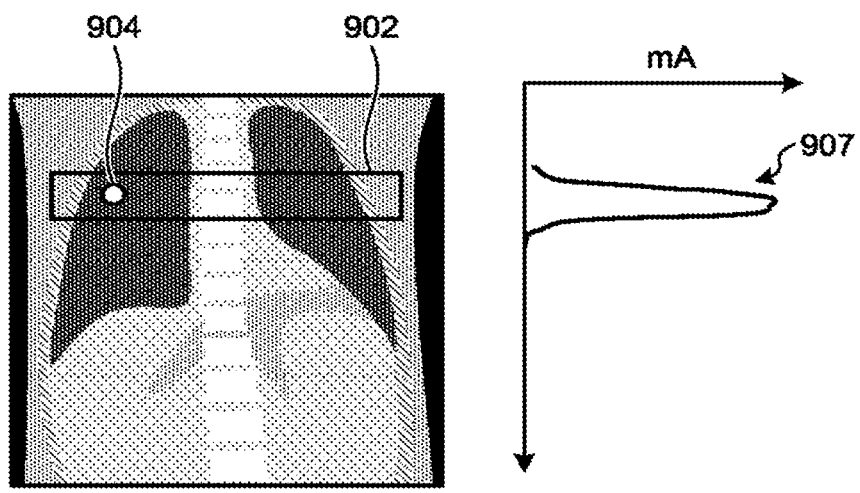
FIG. 2C is a third drawing for explaining the conventional technique.
Figure 2D:
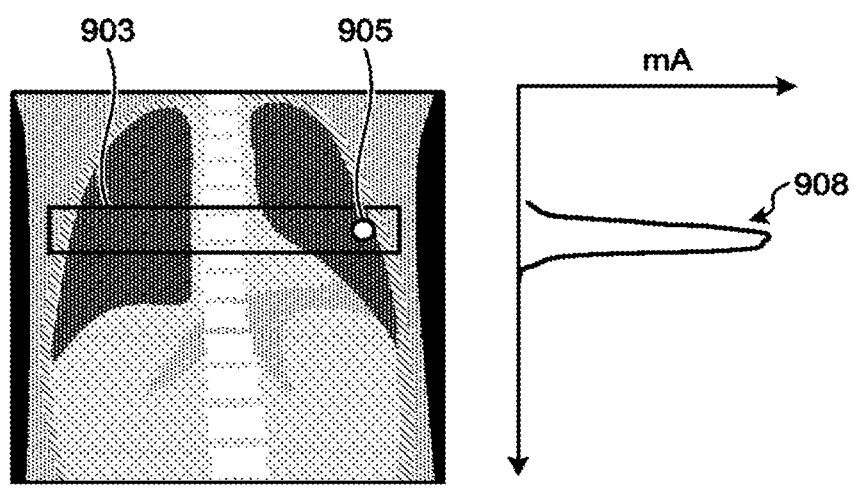
FIG. 2D is a fourth drawing for explaining the conventional technique.

The left section of FIG. 2B illustrates the region 901, whereas the right section of FIG. 2B illustrates a data acquiring condition for the region 901. As illustrated in the right section of FIG. 2B, a data acquiring condition 906 by which the entire chest is imaged by using an ultra-low radiation dose is set as a plan A. For example, in the plan A, the Computed Tomography Dose Index (CTDI) value is equal to or smaller than 3 mGy. Further, the left section of FIG. 2C illustrates the region 902, whereas the right section of FIG. 2C illustrates a data acquiring condition for the region 902. As illustrated in the right section of FIG. 2C, a data acquiring condition 907 by which the lesion site 904 is imaged by using a normal radiation dose is set as a plan B. For example, in the plan B, the CTDI value is approximately 15 mGy. Further, the left section of FIG. 2D illustrates the region 903, whereas the right section of FIG. 2D illustrates a data acquiring condition for the region 903. As illustrated in the right section of FIG. 2D, a data acquiring condition 908 by which the lesion site 905 is imaged by using a normal radiation dose is set as a plan C. For example, in the plan C, the CTDI value is approximately 15 mGy.

After that, as a result of a scan performed according to the plan A, an image of the entire chest is reconstructed. As a result of a scan performed according to the plan B, a high precision image including the lesion site 904 is reconstructed. As a result of a scan performed according to the plan C, a high precision image including the lesion site 905 is reconstructed. In this manner, the X-ray CT apparatus according to the conventional technique reconstructs the images by using the pieces of data acquired by performing the scan for each of the medical examinations. Accordingly, the radiation exposure amount of the patient P increases. The radiation amount (i.e., the CTDI value) totaling the plans A, B, and C is equal to approximately 33 mGy.

To cope with this situation, the X-ray CT apparatus 1 according to the first embodiment is configured to set a third plan for the patient P by integrating together a first plan for the patient P and a second plan for the patient P. For example, the X-ray CT apparatus 1 according to the first embodiment sets a data acquiring condition for a main scan performed on an examined site of the patient P including a region of interest, on the basis of first scan conditions including a data acquiring condition for the examined site of the patient P and second scan conditions including a data acquiring condition for the region of interest included in the examined site. After that, the X-ray CT apparatus 1 according no the first embodiment reconstructs an image under an image reconstruction condition included in the first scan conditions and an image under an image reconstruction condition included in the second scan conditions, by using the pieces of data acquired by using the set data acquiring conditions. The functions described above are realized by the setting function 37b and the reconstructing function 37c. In the following sections, the setting function 37b and the reconstructing function 37c will be explained.

FIG. 3 is a flowchart illustrating a processing procedure performed by the X-ray CT apparatus 1 according to the first embodiment. FIG. 3 illustrates the flowchart for explaining operations of the entire X-ray CT apparatus 1, while explaining which step in the flowchart corresponds to each of the constituent elements. The processes illustrated in FIG. 3 performed by the X-ray CT apparatus 1 according to the first embodiment are, for example, performed as a main scan after a position determining scan is finished, during a follow-up procedure based on a CT image related to a past medical examination.

Step S101 is a step realized by the input circuitry 31. At step S101, the input circuitry 31 receives scan conditions of each of the plans. For example, the input circuitry 31 receives scan conditions for imaging the entire chest, as the plan A. Further, the input circuitry 31 receives scan conditions for imaging a lesion site in the chest as the plan B. In this situation, the scan conditions include a data acquiring condition and an image reconstruction condition.

Step S102 is a step corresponding to the obtaining function 37a. As a result of the processing circuitry 37 invoking and executing a predetermined program corresponding to the obtaining function 37a from the storage circuitry 35, the obtaining function 37a is realized. At step S102, the obtaining function 37a obtains the scan conditions of each of the plans. For example, the obtaining function 37a obtains the scan conditions of the plan A and the plan B received at step S101.

Figure 4A:
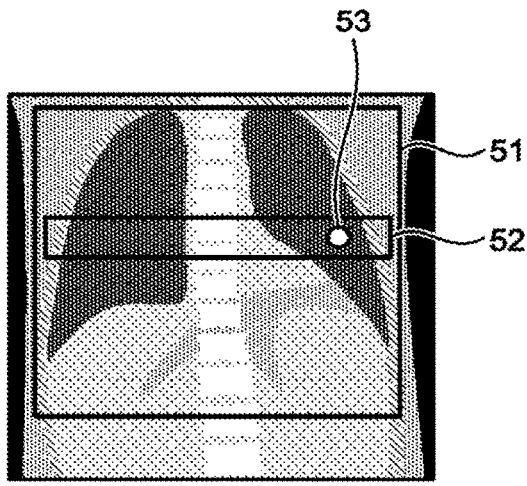
FIG. 4A is a first drawing for explaining a processing operation performed by an obtaining function according to the first embodiment.
Figure 4B:
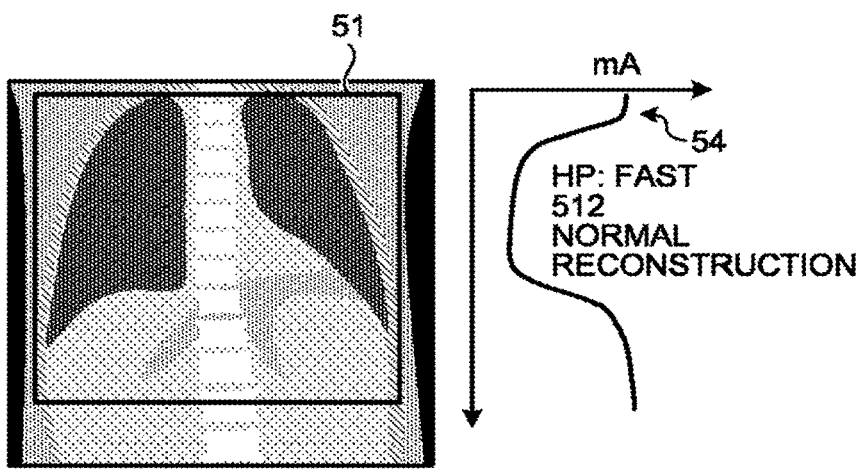
FIG. 4B is a second drawing for explaining the processing operation performed by the obtaining function according to the first embodiment.
Figure 4C:
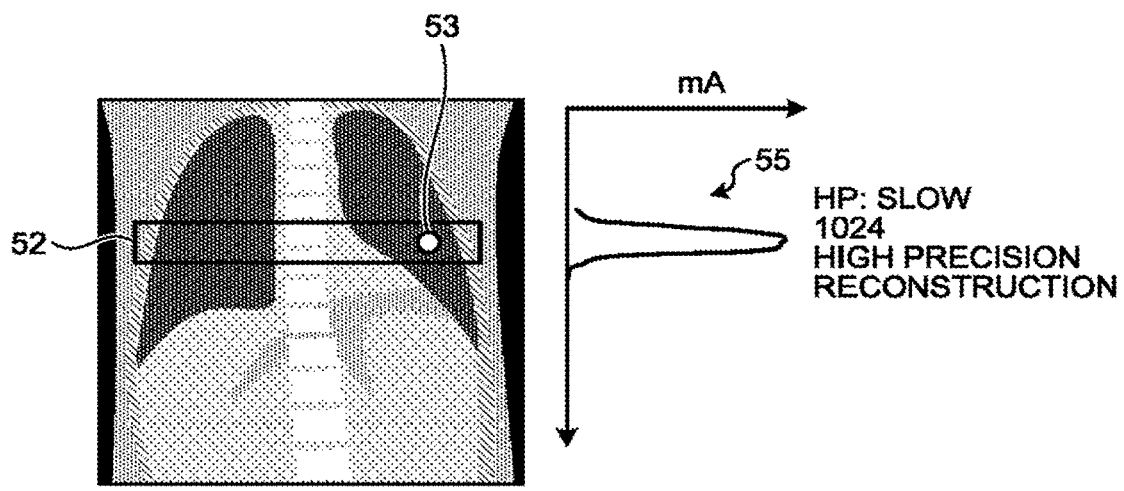
FIG. 4C is a third drawing for explaining the processing operation performed by the obtaining function according to the first embodiment.

Next, a processing operation performed by the obtaining function 37a will be explained with reference to FIGS. 4A to 4C. FIGS. 4A to 4C are drawings for explaining the processing operation performed by the obtaining function 37a according to the first embodiment. FIG. 4A illustrates an image taking area 51 of the plan A and an image taking area 52 of the plan B. As illustrated in FIG. 4A, the image taking area 51 of the plan A is the entire chest. The image taking area 52 of the plan B includes a lesion site 53 serving as a region of interest.

The left section of FIG. 4B illustrates the image taking area 51 of the plan A. The right section of FIG. 4B illustrates the scan conditions of the plan A. As the scan conditions, the obtaining function 37a obtains a data acquiring condition 54 and an image reconstruction condition illustrated in the right, section of FIG. 4B. As illustrated in the right section of FIG. 4B, the data acquiring condition 54 by which the entire chest is imaged by using an ultra-low radiation dose is set in the plan A. In the present example, the data acquiring condition 54 of the plan A includes "Helical Pitch (HP): fast", whereas the image reconstruction condition of the plan A includes, for example, "Display Field Of View (DFOV): Matrix Size 512; Reconstruction Mode: Normal Reconstruction". In this situation, the term "Normal Reconstruction" denotes reconstructing an image by using a detection signal detected by a conventional detector in which detecting elements are arranged in 80 rows corresponding to 896 channels, for example. Although FIG. 4B illustrates the example in which the X-ray tube current is modulated, possible embodiments are not limited to this example. For instance, a data acquiring condition by which the X-ray tube current is kept constant may be set, similarly to the example in the right section of FIG. 2B. The helical pitch may be adjusted, for example, by adjusting the moving speed of the couchtop 22.

The left section of FIG. 4C illustrates the image taking area 52 of the plan B. The right section of FIG. 4C illustrates the scan conditions of the plan B. As the scan conditions, the obtaining function 37a obtains a data acquiring condition 55 and an image reconstruction condition illustrated in the right section of FIG. 4C. As illustrated in the right section of FIG. 4C, the data acquiring condition 55 by which an imaging process is performed by using a normal radiation dose in the position corresponding to the region of interest is set in the plan B. In the present example, the data acquiring condition 55 of the plan B includes "HP: slow", whereas the image reconstruction condition of the plan B includes, for example, "DFOV: Matrix Size 1024; Reconstruction Mode: High Precision Reconstruction" under which an image is to be reconstructed with a higher precision than in the plan A. In this situation, the term "High Precision Reconstruction" denotes reconstructing an image by using a detection signal detected by the detector 13 in which detecting elements are arranged in the 160 rows corresponding to the 1792 channels, for example.

Returning to the description of FIG. 3, step S103 is a step corresponding to the setting function 37b. As a result of the processing circuitry 37 invoking and executing a predetermined program corresponding to the setting function 37b from the storage circuitry 35, the setting function 37b is realized. At step S103, the setting function 37b obtains position information of the region of interest on the basis of either the position determining image or the CT image related to the past medical examination performed on the patient P and further sets a data acquiring condition for the main scan.

Figure 5:
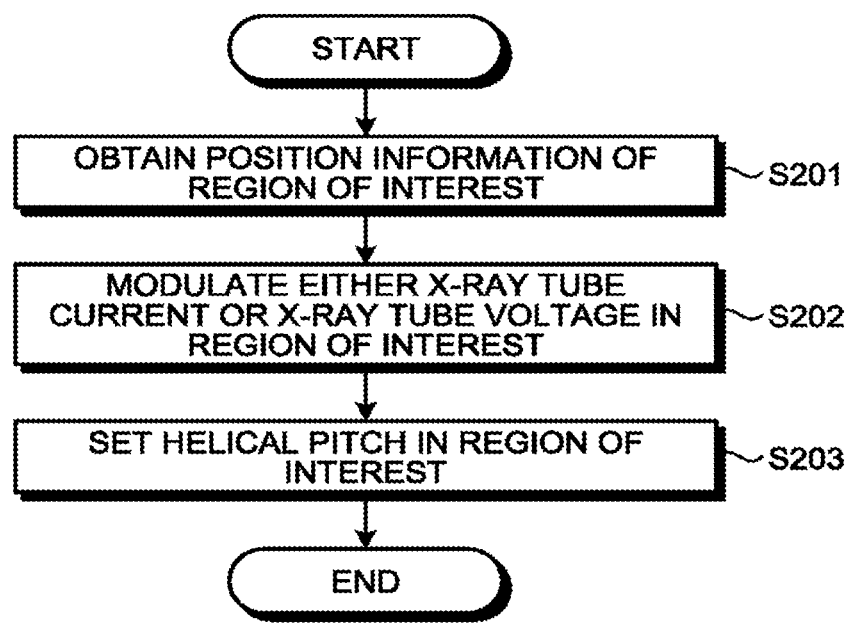
FIG. 5 is a flowchart illustrating a processing procedure performed by a setting function according to the first embodiment.
Figure 6A:
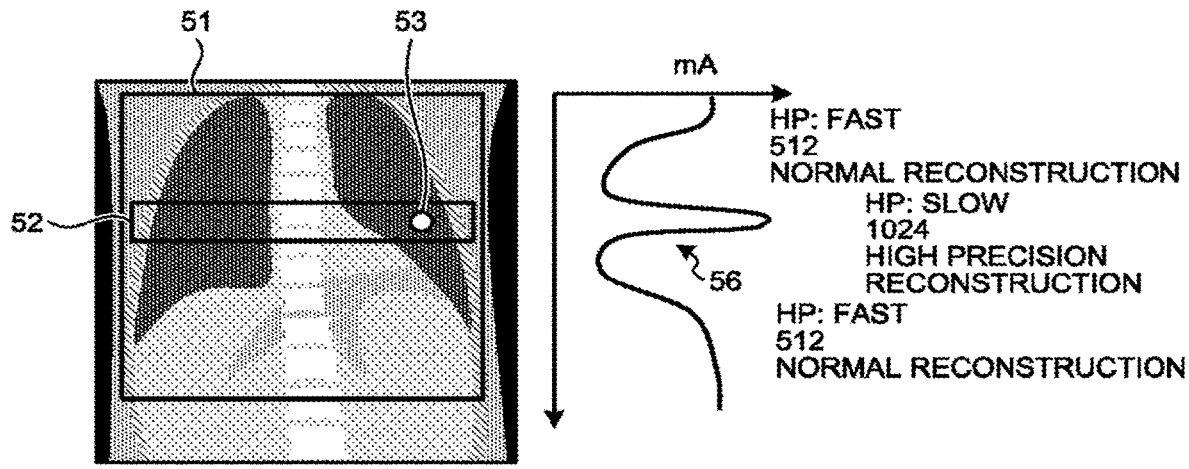
FIG. 6A is a first drawing for explaining a processing operation performed by the setting function according to the first embodiment.
Figure 6B:
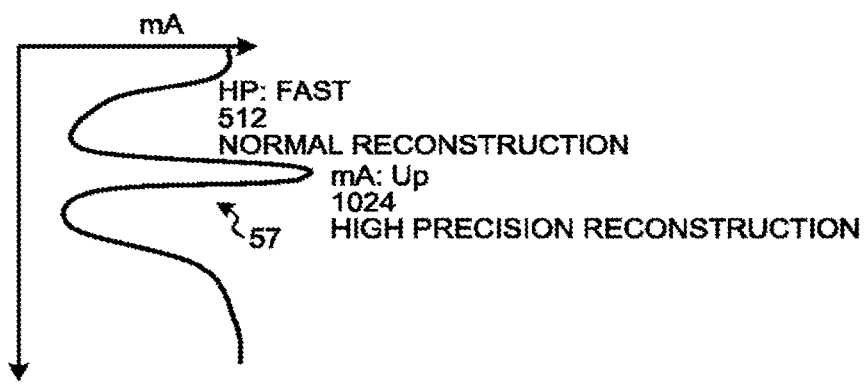
FIG. 6B is a second drawing for explaining the processing operation performed by the setting function according to the first embodiment.

Next, details of the process performed by the setting function 37b at step S103 will be explained, with reference to FIGS. 5, 6A, and 6B. FIG. 5 is a flowchart illustrating a processing procedure performed by the setting function 37b according to the first embodiment. FIGS. 6A and 6B are drawings for explaining a processing operation performed by the setting function 37b according to the first embodiment.

The processing procedure illustrated in FIG. 5 corresponds to the process at step S103 in FIG. 3. Steps S201 through S203 in FIG. 5 are steps corresponding to the setting function 37b. As a result of the processing circuitry 37 invoking and executing a predetermined program corresponding to the setting function 37b from the storage circuitry 35, the setting function 37b is realized.

At step S201, the setting function 37b obtains the position information of the region of interest. For example, the setting function 37b obtains the position information of the region of interest, on the basis of either the position determining image or the CT image related the past medical examination performed on the patient P. In one example, as illustrated in the left section of FIG. 6A, the setting function 37b obtains position information of the lesion site 53 detected in the CT image related to a past medical examination performed on the patient P. In other words, the region of interest is the region including the lesion site in either the position determining image of the patient P or the CT image related to the past medical examination performed on the patient P.

At step S202, the setting function 37b modulates either the X-ray tube current or the X-ray tube voltage in the region of interest. In this situation, for example, the setting function 37b puts together the data acquiring condition 54 of the plan A and the data acquiring condition 55 of the plan B obtained at step S102, into one data acquiring condition 56. The data acquiring condition 56 illustrated in the right section of FIG. 6A is a data acquiring condition implemented in a helical scan. More specifically, as illustrated in the right section of FIG. 6A, the setting function 37b modulates the X-ray tube current in the data acquiring condition 54 of the plan A, in such a manner that an imaging process is performed by using a normal radiation dose in the position of the lesion site 53 obtained at step S201. In that situation, the X-ray tube current in the position of the lesion site 53 is equal to the X-ray tube current in the data acquiring condition 55 of the plan B. In this manner, the setting function 37b sets the data acquiring condition for the main scan by which either the X-ray tube current or the X-ray tube voltage in the region of interest is modulated in comparison to that in the region other than the region of interest.

At step S203, the setting function 37b sets a helical pitch in the region of interest. For example, as illustrated in the right section of FIG. 6A, the setting function 37b sets the data acquiring condition 56 in such a manner that the helical pitch is slower in the position of the lesion site 53, for the purpose of enhancing the spatial resolution of the lesion site 53 obtained at step S201. In other words, the setting function 37b sets the data acquiring condition of the main scan by which the helical pitch in the region of interest is at a lower speed than that in the region other than the region of interest. As a result, the helical pitch in the position of the lesion site 53 is slower than the helical pitch in any position other than the lesion site 53. In this manner, the setting function 37b sets the data acquiring condition of the plan obtained by integrating the plan A and the plan B together. In the following sections, the plan A, may also be referred to as a first plan, whereas the plan B may also be referred to as a second plan. The plan obtained by integrating the plan A and the plan B together may be referred to as a third plan.

Alternatively, as illustrated in FIG. 6B, for the purpose of enhancing the special resolution of the lesion site 53, the setting function 37b may set a data acquiring condition 57 by which the X-ray tube current is further increased without changing the helical pitch in the position of the lesion site 53. In this manner, the setting function 37b sets the third plan for the patient P, by integrating together the first plan for the patient P and the second plan for the patient P. For example, the setting function 37b sets the data acquiring condition for the main scan performed on the examined site of the patient P including the region of interest, on the basis of the first scan conditions including the data acquiring condition for the examined site of the patient P and the second scan conditions including the data acquiring condition for the region of interest included in the examined site. In other words, the setting function 37B sets the third plan for the imaging target site of the patient P including the region of interest, by integrating together the first plan for the imaging target site of the patient P and the second plan for the region of interest included in the imaging target site.

Returning to the description of FIG. 3, step S104 is a step realized by the processing circuitry 37. At step S104, the processing circuitry 37 causes the display 32 to display the data acquiring condition set at step S103.

Step S105 is a step realized by the processing circuitry 37. At step S105, the processing circuitry 37 judges whether or not an instruction to perform the main scan has been received. When it is determined that an instruction to perform the main scan has been received (step S105: Yes), the processing circuitry 37 proceeds to step S106.

Step S106 is a step realized by the scan controlling circuitry 33. At step S106, the scan controlling circuitry 33 performs a scan. For example, under the control of the processing circuitry 37, the scan controlling circuitry 33 controls the projection data acquiring process performed by the gantry 10 by using the data acquiring condition set at step S103, by controlling operations of the X-ray radiation controlling circuitry 11, the gantry driving circuitry 16, the data acquiring circuitry 14, and the couch driving device 21. As a result, according to the third plan, the detector 13 detects high precision detection data output from the detecting elements arranged in the 160 rows corresponding to the 1792 channels.

Step S107 is a step corresponding to the reconstructing function 37c. As a result of the processing circuitry 37 invoking and executing a predetermined, program corresponding to the reconstructing function 37c from the storage circuitry 35, the reconstructing function 37c is realized. At step S107, the reconstructing function 37c reconstructs images on the basis of the scan conditions of the plans. In other words, by using the pieces of data acquired under the set data acquiring conditions, the reconstructing function 37c reconstructs an image under the image reconstruction condition included in the first scan conditions and an image under the image reconstruction condition included in the second scan conditions. For example, the reconstruction function 37c reconstructs an image under the image reconstruction condition of the plan A, while using the data acquired at step S106. Further, the reconstructing function 37c reconstructs an image under the image reconstruction condition of the plan B, while using the data acquired at step S106.

In this situation, the reconstructing function 37c reconstructs a first image and a second image having mutually-different resolutions. For example, from the data corresponding to a first resolution, which is a high precision resolution, and having been acquired according to the third plan obtained by integrating the plan A and the plan B together, the reconstructing function 37c generates the first image and the second image of which one of the two resolutions is equal to the first resolution, whereas the other resolution is equal to a second resolution lower than the first resolution. More specifically, the reconstructing function 37c reconstructs the image having the first resolution when the reconstruction mode is set to a high precision reconstruction mode and reconstructs the image having the second resolution when the reconstruction mode is set to a normal reconstruction mode.

For example, the reconstructing function 37c reconstructs the image having the first resolution from the data acquired according to the third plan and reconstructs the image having the second resolution from data obtained by bundling the data acquired according to the third plan so as to have the second resolution. In one example, because the reconstruction mode in the image reconstruction condition of the plan A is set to the normal reconstruction mode, the reconstructing function 37c reconstructs the image having the second resolution. In this situation, the projection data acquired according to the third plan is projection data based on the high precision detection data detected by the detecting elements arranged in the 160 rows corresponding to the 1792 channels. Accordingly, the reconstructing function 37c bundles the high precision projection data to perform a normal reconstruction process. For example, the reconstructing function 37c puts together every four detecting elements as one unit and further adds together pieces of high precision projection data corresponding to the four detecting elements combined in one unit. After that, the reconstructing function 37c reconstructs an image corresponding to the image taking area of the plan A from the projection data resulting from the addition.

Further, because the reconstruction mode in the image reconstruction condition of the plan B is set to the high precision reconstruction mode, the reconstructing function 37c reconstructs the image having the first resolution. From the high precision projection data acquired according to the third plan, the reconstructing function 37c reconstructs an image corresponding to the image taking area of the plan B.

Alternatively, when generating the images having the mutually-different resolutions, the reconstructing function 37c may generate an image having the lower resolution by performing an image processing process, instead of generating an image having the lower resolution by bundling the high precision projection data. For example, from the high precision projection data acquired according to the third plan, the reconstructing function 37c reconstructs the first image and the second image of which the resolutions are each equal to the first resolution and further performs an image processing process so that the resolution of one of the first and the second images becomes equal to the second resolution. More specifically, from the high precision projection data acquired according to the third plan, the reconstructing function 37c reconstructs an image (an image A) corresponding to the image taking area of the plan A and another image (an image B) corresponding to the image taking area of the plan B. After that, the reconstructing function 37c generates an image having the lower resolution by putting together every four pixels in the image A into one unit.

Step S108 is a step realized by the processing circuitry 37. At step S108, the processing circuitry 37 causes the display 32 to display the images of the plans reconstructed at step S107. For example, the processing circuitry 37 causes the display 32 to display the image of the plan A and the image of the plan B. Alternatively, the processing circuitry 37 causes the display 32 to display a combined image obtained by combining together the image of the plan A and the image of the plan B. In another example, the processing circuitry 37 causes the display 32 to display the image of the plan A, the image of the plan B, and a combined image obtained by combining together the image of the plan A and the image of the plan B.

Further, at step S105, when it is determined that the instruction to perform the main, scan has not been received (step S105: No), the processing circuitry 37 proceeds to step S109. Steps S109 through S111 are steps realized by the processing circuitry 37. At step S109, the processing circuitry 37 judges whether or not a request to edit the plans has been received. In this situation, when it is determined that a request to edit the plans has been received (step S109: Yes), the processing circuitry 37 proceeds to step S110.

At step S110, the processing circuitry 37 receives an operation to edit the plans. For example, as a result of the operator performing an operation to edit any of the image taking areas by using a GUI, the processing circuitry 37 receives the operation to edit the plans. In this situation, the processing circuitry 37 may receive an editing operation for each of the plans received at step S101. Alternatively, the processing circuitry 37 may receive an editing operation applied to the plans after the data acquiring condition is set at step S103. Details of the process performed by the processing circuitry 37 at step S110 will be explained with reference to FIGS. 6C to 6F. FIGS. 6C to 6F are drawings for explaining a processing operation performed by the processing circuitry 37 according to the first embodiment.

Figure 6C:
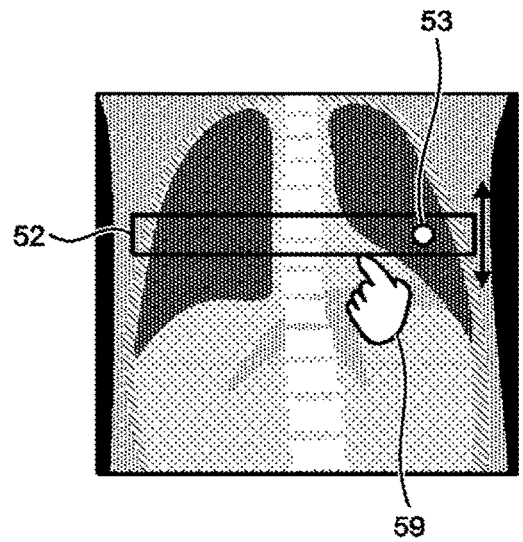
FIG. 6C is a first drawing for explaining a processing operation performed by processing circuitry according to the first embodiment.
Figure 6D:
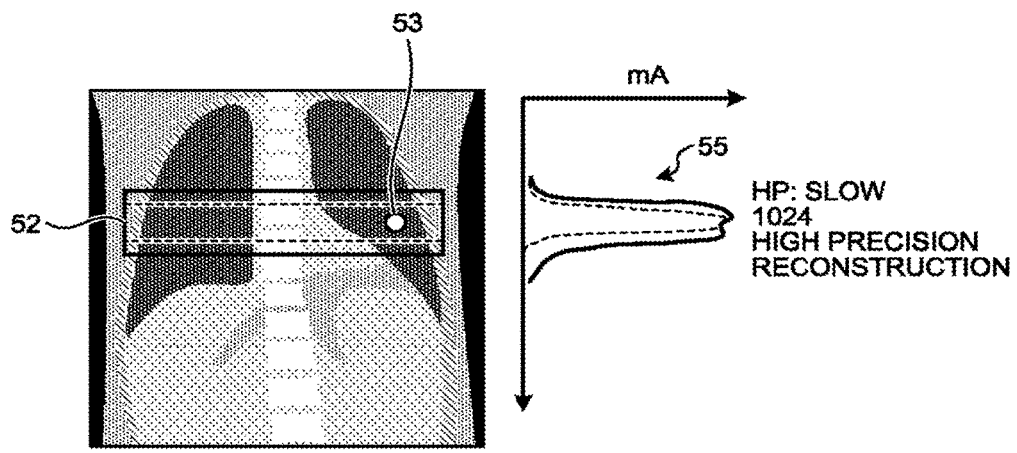
FIG. 6D is a second drawing for explaining the processing operation performed by the processing circuitry according to the first embodiment.

With reference to FIGS. 6C and 6D, a first editing mode in which an editing operation is received for each of the plans will be explained. FIG. 6C illustrates an example in which an editing operation performed on the image taking area 52 of the plan B is received, without receiving any editing operation performed on the image taking area 51 of the plan A. In other words, the processing circuitry 37 temporarily disassembles the integrated image taking areas and changes only the image taking area 52. For example, as illustrated in FIG. 6C, the display 32 displays an image rendering the image taking area 52 of the plan B. In this situation, for example, let us assume that the operator stretches the image taking area 52 in the directions indicated by the bi-directional arrow by manipulating a finger icon 59. As a result, the processing circuitry 37 determines that an operation to stretch the image taking area 52 of the plan B has been received and changes the image taking area 52 as illustrated in the left section of FIG. 6D. In the left section of FIG. 6D, the image taking area 52 before the change is indicated with the broken line, whereas the image taking area 52 after the change is indicated with the solid line. Although the example is explained in which the operator stretches the image taking area 52 in the directions indicated by the bi-directional arrow by manipulating the finger icon 59, possible embodiments are not limited to this example. Another example is also acceptable in which the operator stretches the image taking area 52 only in a single direction designated by a manipulation applied to the finger icon 59.

Figure 6E:
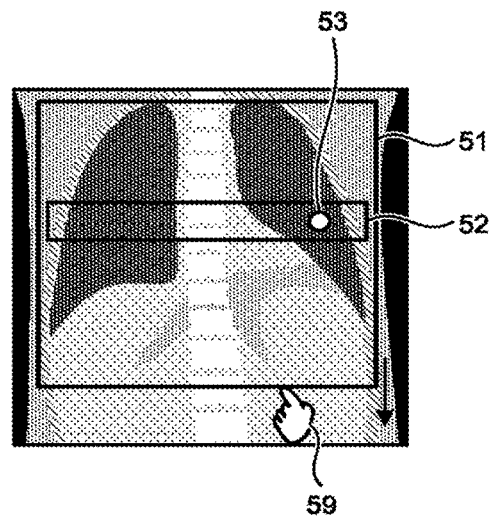
FIG. 6E is a third drawing for explaining the processing operation performed by the processing circuitry according to the first embodiment.
Figure 6F:
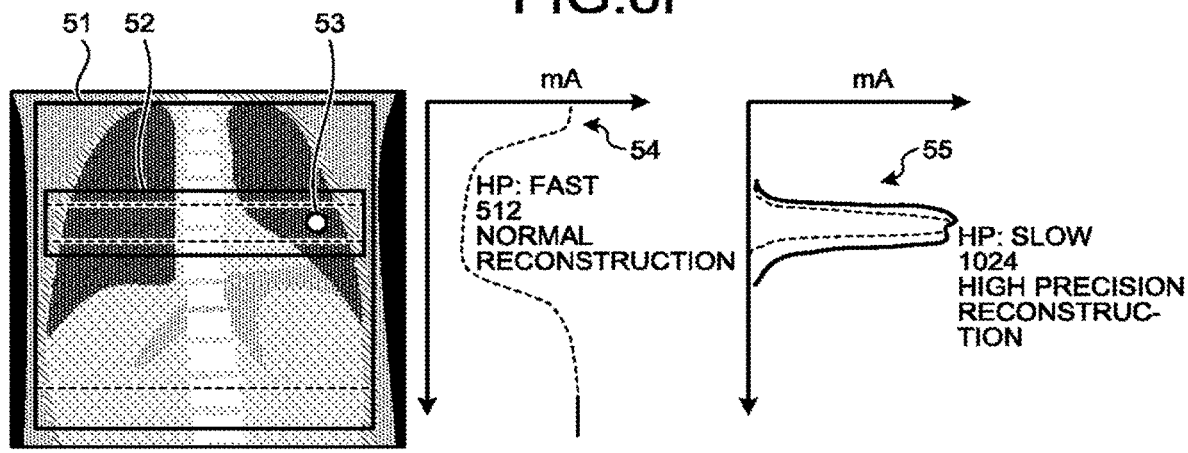
FIG. 6F is a fourth drawing for explaining the processing operation performed by the processing circuitry according to the first embodiment.

Next, with reference to FIGS. 6E and 6F, a second editing mode will be explained in which an editing operation is received with respect to a plan obtained by integrating together the plan. A and the plan B. For example, as illustrated in FIG. 6E, the display 32 displays an image rendering the image talking area 51 and the image talking area 52 of the plan obtained by integrating the plan A and the plan B together. In this situation, for example, let us assume that, the operator stretches the image taking area 51 in the direction indicated by the arrow, by manipulating the finger icon 59. In that situation, the processing circuitry 37 determines that an operation to stretch both the image taking area 51 and the image taking area 52 of the integrated plan has been received. Accordingly, the processing circuitry 37 changes the image taking area 51 and the image taking area 55, as illustrated in the left section of FIG. 6F. In other words, the processing circuitry 37 integrally changes the image taking area 51 and the image taking area 52, without disassembling the integrated image taking areas. In the left section of FIG. 6F, the image taking area 51 and the image taking area 52 before the change are indicated with the broken lines, whereas the image taking area 51 and the image taking area 52 after the change are indicated with the solid lines. In other words, when having received an operation to edit one of the image taking areas of the integrated plan, the processing circuitry 37 changes all the image taking areas included in the integrated plan at the same time.

Returning to the description of FIG. 3, at step S111, the processing circuitry 37 revises the scan conditions of the plan for which the editing operation has been received. For example, when having received editing operations in units of plans, the processing circuitry 37 revises the scan conditions of each of the plans for which the editing operation has been received. In one example, when having received editing operations in units of plans, the processing circuitry 37 changes the scan conditions as indicated in the right section of FIG. 6D. More specifically, in the right section of FIG. 6D, the data acquiring condition 55 of the plan B before the change is as indicated with the broken line, whereas the data acquiring condition 55 of the plan B after the change is as indicated with the solid line.

Further, for example, when having received an editing operation to edit the integrated plan, the processing circuitry 37 revises the scan conditions in units of plans that are included in the integrated plan. In one example, when having received an editing operation to edit the integrated plan, the processing circuitry 37 changes the scan conditions as indicated in the middle and the right sections of FIG. 6F. More specifically, in the middle section of FIG. 6F, the data acquiring 54 of the plan A before the change is as indicated with the broken line, whereas the data acquiring condition 54 of the plan A after the change is as indicated with the solid line. Further, in the right section of FIG. 6F, the data acquiring condition 55 of the plan B before the change is indicated with the broken line, whereas the data acquiring condition 55 of the plan B after the change is indicated with the solid line. After the process at step S111 is finished, the obtaining function 37a obtains the scan conditions of the plans at step S102. Further, when having received an operation to edit the plans through a manipulation applied to the data acquiring conditions of the integrated plan at step S110, the processing circuitry 37 revises the scan conditions at step S111 and subsequently proceeds to step S104 by skipping steps S102 and S103.

Returning to the description of FIG. 3, when having determined at step S109 that no request to edit the plans has been received (step S109: No), the processing circuitry 37 proceeds to step S112. At step S112, the processing circuitry 37 judges whether or not a cancellation has been received. In this situation, when it is determined that a cancellation has been received (step S112: Yes), the processing circuitry 37 ends the process. On the contrary, when it is determined that no cancellation has been received (step S112: No), the processing circuitry 37 keeps repeatedly performing the judging process at step S105.

Although the example is explained with reference to FIGS. 6C to 6F in which the processing circuitry 37 receives the operation to edit the plans by receiving the operation to edit the image taking areas through the GUI, for example, possible embodiments are not limited to this example. For instance, the processing circuitry 37 may receive an operation to edit the plans by receiving an operation to edit any of the data acquiring conditions. In that situation, the processing circuitry 37 may receive an operation to edit the data acquiring condition in the graph illustrated in the right section of FIG. 6D. Alternatively, the processing circuitry 37 may receive an operation to edit a data acquiring condition that is set as a numerical value indicating an X-ray tube current, an X-ray tube voltage, or the like. Further, when having received an operation to edit a data acquiring condition in a graph, the processing circuitry 37 may change the data acquiring condition that is set as a numerical value. Alternatively, when having received an operation to edit a data acquiring condition that is set as a numerical value, the processing circuitry 37 may change the shape of the graph. Further, in synchronization with the operation to edit the data acquiring condition, the processing circuitry 37 may change the image taking region displayed by the GUI.

Further, the processing circuitry 37 may arrange the first editing mode and the second editing mode described above to be switchable with each other. Further, in accordance with the switching between the first editing mode and the second editing mode, the processing circuitry 37 may display only an editable image taking area while arranging an uneditable image taking area to be in a non-display state or may display the uneditable image taking area, too, while keeping it impossible to receive an editing operation thereon. Further, similarly with respect to the data acquiring condition that is set as a numerical value or the data acquiring condition indicated in the graph, the processing circuitry 37 may, in accordance with the switching between the first editing mode and the second editing mode, display only an editable acquiring condition or may display an uneditable data acquiring condition, too, while keeping it impossible to receive an editing operation thereon.

As explained above, in the first embodiment, the X-ray CT apparatus 1 is configured to set the data acquiring condition of the main scan performed on the examined site of the patient including the region of interest, on the basis of the first scan conditions including the data acquiring condition for the examined site of the patient and the second scan conditions including the data acquiring condition for the region of interest included in the examined site. In this manner, for example, when implementing the two plans that are set independently of each other, the X-ray CT apparatus 1 according to the first embodiment sets the data acquiring condition to perform the imaging process as a single plan, on the basis of the data acquiring conditions of the two plans. With this arrangement, the operator of the X-ray CT apparatus 1 simply needs to press an imaging start button only once. As a result, the operator of the X-ray CT apparatus 1 is able to perform the medical examination more efficiently.

Further, when a region of interest included in an examined site of a patient is imaged after the examined site is imaged, X-rays would be radiated onto the region of interest twice. When the X-ray CT apparatus 1 according to the first embodiment is used, because the data acquiring condition is set so as to perform the imaging process as the single plan, it is possible to reduce the number of times the X-rays are radiated onto the region of interest. As explained herein, according to the first embodiment, it is possible to reduce the radiation exposure.

Further, when the X-ray CT apparatus according to the conventional technique is used, because it is necessary to perform the imaging process multiple times, the patient needs to be restrained for a long period of time. In contrast, when the X-ray CT apparatus according to the first embodiment is used, because it is possible to reduce the number of times the imaging process is performed, it is possible to shorten the time period for which the patient needs to be restrained. As a result, according to the first embodiment, it is possible to reduce the burden on the patient.

First Modification Example of First Embodiment

In the embodiment described above, the example is explained in which the examined site includes the one lesion site; however, possible embodiments are not limited to this example. For instance, a plurality of lesion sites may be present in an examined site. Even when a plurality of lesion sites are present in an examined site, the X-ray CT apparatus 1 performs the processing procedure illustrated in FIG. 3. In the following sections, operations performed by the obtaining function 37a and the setting function 37b according to a modification example of the first embodiment will be explained with reference to FIGS. 7A to 7E. FIGS. 7A to 7E are drawings for explaining a first modification example of the first embodiment.

Figure 7A:
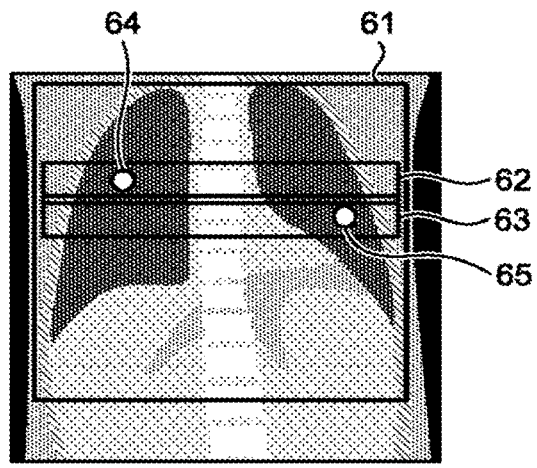
FIG. 7A is a first drawing for explaining a modification example of the first embodiment.

FIG. 7A illustrates an example in which the entire chest, a lesion site 64, and a lesion site 65 are to be imaged. More specifically, as the plan A, a region 61 is set as an image taking area for the entire chest. As the plan B, a region 62 is set as an image taking area including the lesion site 64. As the plan C, a region 63 is set as an image taking area including the lesion site 65. In the example in FIG. 7A, the obtaining function 37a obtains the scan conditions of the plan A, the plan B, and the plan C.

Figure 7B:
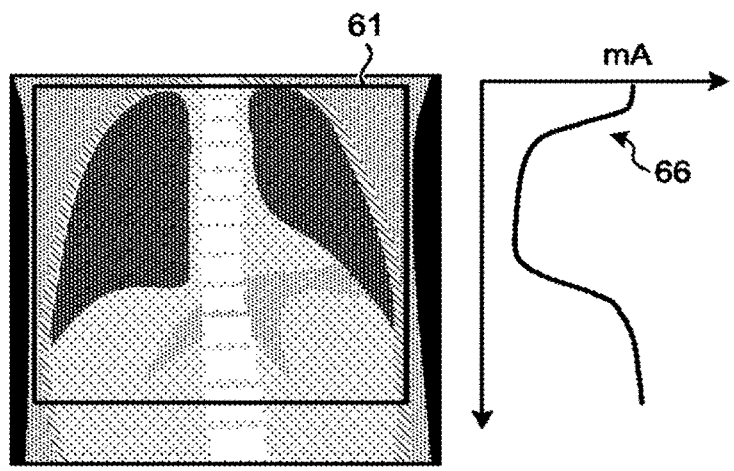
FIG. 7B is a second drawing for explaining the modification example of the first embodiment.

The left section of FIG. 7B illustrates the image taking area 61 of the plan A, whereas the right section of FIG. 7B illustrates a scan conditions of the plan A. As the scan conditions, the obtaining function 37a obtains a data acquiring condition 66 illustrated in the right section of FIG. 7B and an image reconstruction condition. As illustrated in the right section of FIG. 7B, in the plan A, the data acquiring condition 66 is set by which the entire chest is imaged by using an ultra-low radiation dose. In this situation, the data acquiring condition 66 of the plan A includes "HP: fast", whereas the image reconstruction condition of the plan A includes, for example, "DFOV: Matrix Size 512; Reconstruction Mode: Normal Reconstruction". Although FIG. 7B illustrates the example in which the X-ray tube current is modulated, possible embodiments are not limited to this example. For instance, similarly to the example in the right section of FIG. 2B, a data acquiring condition by which the X-ray tube current is constant may be set.

Figure 7C:
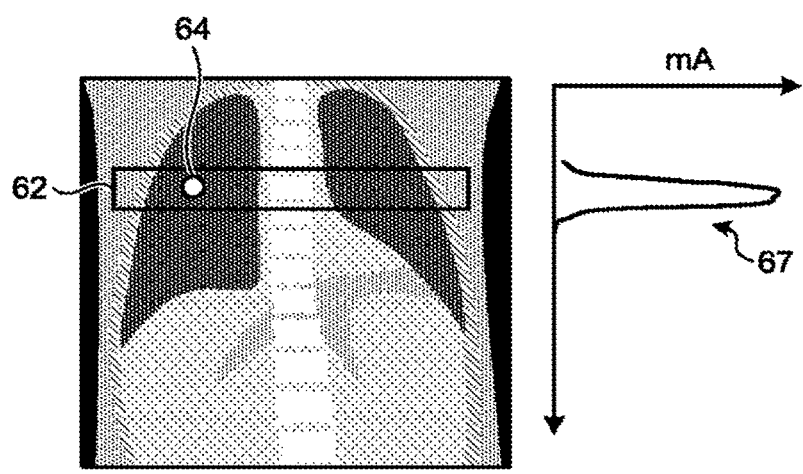
FIG. 7C is a third drawing for explaining the modification example of the first embodiment.

The left section of FIG. 7C illustrates the image taking area 62 of the plan B, whereas the right section of FIG. 7C illustrates a scan condition of the plan B. As the scan conditions, the obtaining function 37a obtains a data acquiring condition 67 illustrated in the right section of FIG. C and an image reconstruction condition. As illustrated in the right section of FIG. 7C, in the plan B, the data acquiring condition 67 is set by which an imaging process is performed by using a normal radiation dose in the position corresponding to the region of interest. In this situation, the data acquiring condition 67 of the plan B includes "HP: slow", whereas the image reconstruction condition of the plan B includes, for example, "DFOV: Matrix Size 1024; Reconstruction Mode: High Precision Reconstruction".

Figure 7D:
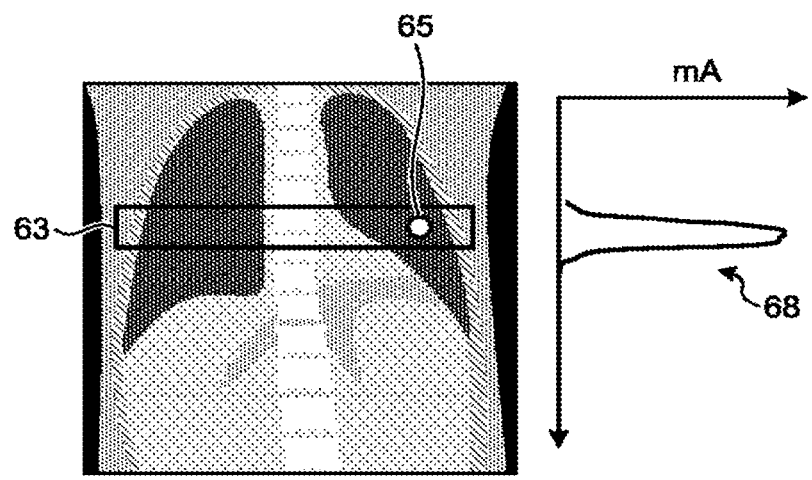
FIG. 7D is a fourth drawing for explaining the modification example of the first embodiment.

The left section of FIG. 7D illustrates the image taking area 63 of the plan C, whereas the right section of FIG. 7D illustrates a scan condition of the plan C. As the scan conditions, the obtaining function 37a obtains a data acquiring condition 68 illustrated in the right section of FIG. 7D and an image reconstruction condition. As illustrated in the right section of FIG. 7D, in the plan C, the data acquiring condition 68 is set by which an imaging process is performed by using a normal radiation dose in the position corresponding to the region of interest. In this situation, the data acquiring condition 68 of the plan C includes "HP: slow", whereas the image reconstruction condition of the plan C includes, for example, "DFOV: Matrix Size 1024; Reconstruction Mode: High Precision Reconstruction".

Further, when a plurality of r eg irons of interest are present, the setting function 37b sets a data acquiring condition of a main scan including the plurality of regions of interest, on the basis of the first scan conditions and the second scan conditions for each of the regions of interest. For example, the setting function 37b puts together the data acquiring condition 66 of the plan A illustrated in FIG. 7B, the data acquiring condition 67 of the plan B illustrated in FIG. 7C, and the data acquiring condition 68 of the plan C illustrated in FIG. 7D into one data acquiring condition 69. Also, when a plurality of lesion sites are present in an examined site, the setting function 37b performs the processing procedure illustrated in FIG. 5.

Figure 7E:
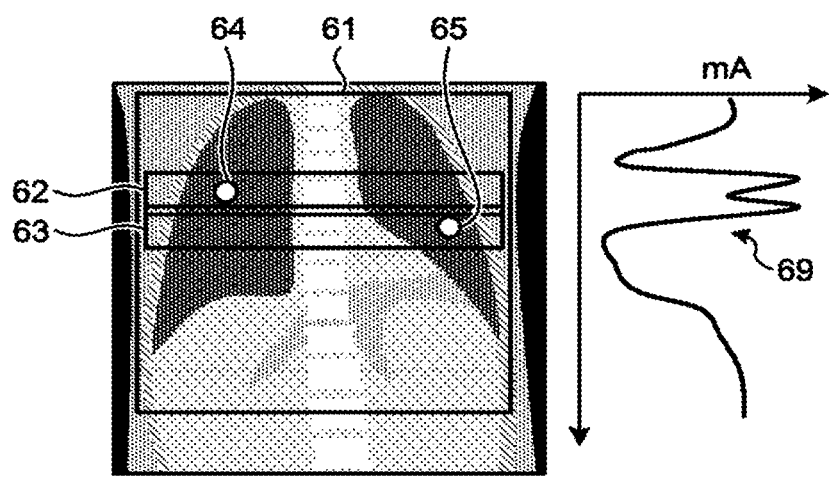
FIG. 7E is a fifth drawing for explaining the modification example of the first embodiment.

The left section of FIG. 7E illustrates the image taking area 61 of the plan A, the image taking area 62 of the plan B, and the image taking area 63 of the plan C. Further, the right section of FIG. 7E illustrates a data acquiring condition 69. The data acquiring condition 69 illustrated in the right section of FIG. 7E is a data acquiring condition implemented in a helical scan. As illustrated in the right section of FIG. 7E, the setting function 37b modulates the X-ray tube current in the data acquiring condition 66 of the plan A, so that an imaging process is performed by using a normal radiation dose in the obtained positions of the lesion site 64 and the lesion site 65. In that situation, the X-ray tube current, in the position of the lesion site 64 is equal to the X-ray tube current in the data acquiring condition 67 of the plan B, whereas the X-ray tube current in the position of the lesion site 65 is equal to the X-ray tube current in the data acquiring condition 68 of the plan C.

Further, the setting function 37b sets helical pitches for the regions of interest. For example, for the purpose of enhancing the spatial resolutions in the lesion site 64 and the lesion site 65 that were obtained, the setting function 37b sets the data acquiring condition 69 in such a manner that the helical pitches are slower in the positions of the lesion site 64 and the lesion site 65. In other words, the helical pitches in the positions of the lesion site 64 and the lesion site 65 are slower than the helical pitch in any position other than the lesion site 64 and the lesion site 65. Alternatively, for the purpose of enhancing the spatial resolutions in the lesion site 64 and the lesion site 65, the setting function 37b may set a data acquiring condition by which the X-ray tube current is further increased, instead of changing the helical pitches in the positions of the lesion site 64 and the lesion site 65.

The reconstructing function 37c reconstructs images each under the image reconstruction condition included in the first scan conditions and under the image reconstruction condition included in the second scan conditions corresponding to each of the regions of interest, while using the data acquired under the set data acquiring condition. Further, the processing circuitry 37 causes the display 32 to display the reconstructed images of the plans. For example, the processing circuitry 37 causes the display 32 to display the image of the plan A, the image of the plan B, and the image of the plan C. Alternatively, the processing circuitry 37 causes the display 32 to display a combined image obtained by combining together the image of the plan A, the image of the plan B, and the image of the plan C. In another example, the processing circuitry 37 causes the display 32 to display the image of the plan A, the image of the plan B, the image of the plan C, and a combined image obtained by combining tougher the image of the plan A, the image of the plan B, and the image of the plan C.

As explained above, in the modification example of the first embodiment, when the plurality of regions of interest are present, the X-ray CT apparatus 1 is configured to set the data acquiring condition of the main scan including the plurality of regions of interest, on the basis of the first scan conditions and the second scan conditions for each of the regions of interest. In this manner, for example, when implementing the three plans that are set independently of each other, the X-ray CT apparatus 1 according to the modification example of the first embodiment sets the data acquiring condition by which the imaging process is performed as the single plan, on the basis of the data acquiring conditions of the three plans. With this arrangement, the operator of the X-ray CT apparatus 1 simply needs to press the imaging start button only once. As a result, the operator of the X-ray CT apparatus 1 is able to perform the medical examination more efficiently.

Further, when regions of interest included in an examined site of a patient are imaged after the examined site of is imaged, X-rays would be radiated onto the regions of interest twice. Further, when a helical scan is to be performed on an image taking area, the imaging process is performed on an area obtained by adding an extra margin to the set image taking area. Accordingly, the X-rays are radiated onto an area larger than the set image talking area. For this reason, when a conventional X-ray CT apparatus is used, when the distance between the regions of interest is short, the X-rays would be radiated onto the extra margin area in duplicate. In contrast, when the X-ray CT apparatus 1 according to the modification example of the first embodiment is used, because the data acquiring condition is set by which the imaging process is performed as the single plan, it is possible to reduce the number of times the X-rays are radiated onto the regions of interest and the extra margin area. As explained herein, according to the modification example of the first embodiment, it is possible to reduce the radiation exposure. More specifically, in contrast to the radiation amount (the CTDI value) of the example in FIGS. 2A to 2D being approximately 33 mGy, the image taking process illustrated in FIG. 7E is able to reduce the CTDI value to approximately 25 mGy.

Second Modification Example of First Embodiment

Figure 8A:
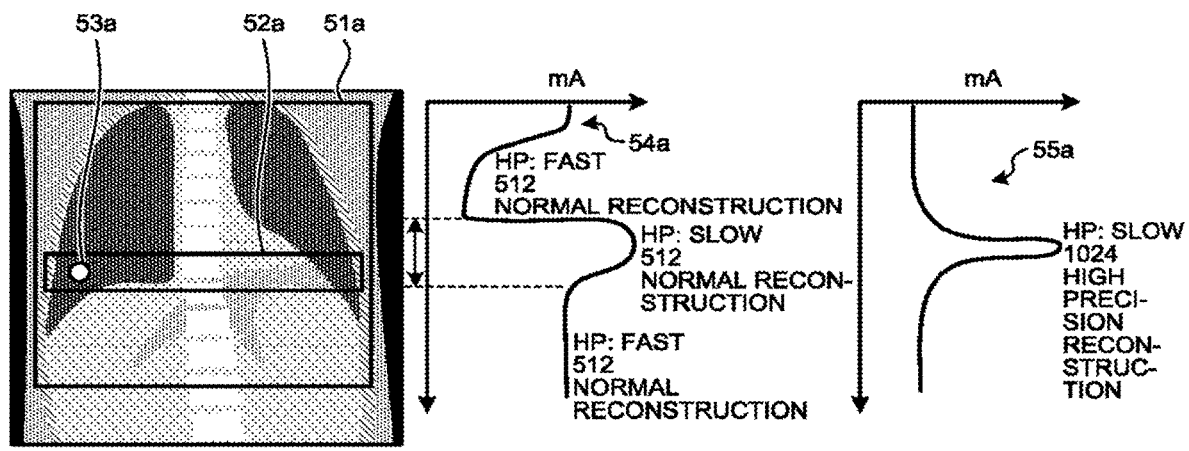
FIG. 8A is a drawing for explaining a second modification example of the first embodiment.
Figure 8B:
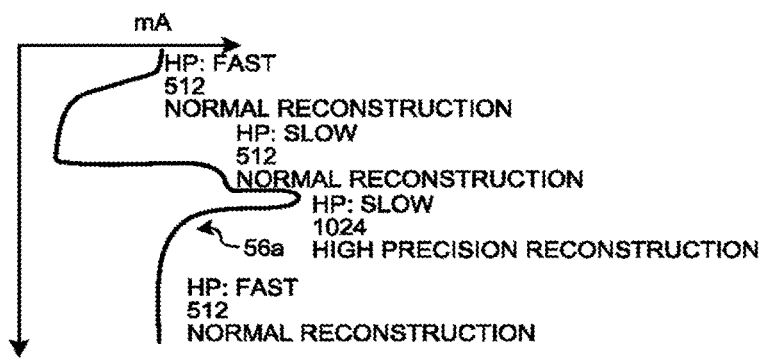
FIG. 8B is another drawing for explaining the second modification example of the first embodiment.

In the first embodiment above, the example is explained in which the entire chest, for example, is imaged according to the plan A, whereas the lesion site of lung cancer or the like, for example, is imaged as the region of interest according to the plan B. In this regard, for example, the first embodiment above is also applicable to a situation where a Variable Helical Pitch (VHP) is used as a plan A. FIGS. 8A and 8B are drawings for explaining a second modification example of the first embodiment.

With reference to FIGS. 8A and 8B, an example will be explained in which, as the plan A, an image of the entire chest is taken by using a VHP so that no impact is made by the pulse and, as a plan B, a lesion site such as lung cancer or the like is imaged as a region of interest. The left section of FIG. 8A illustrates an image taking area 51a of the plan A, an image taking area 52a of the plan B, and a lesion site 53a serving as the region of interest. Further, the middle section of FIG. 8A illustrates scan conditions of the plan A. As one of the scan conditions of the plan A, a data acquiring condition. 54a is set that is obtained by applying a VHP to the data acquiring condition 54 by which the entire chest is imaged while using an ultra-low radiation dose illustrated in FIG. 4B. For example, the data acquiring condition 54a adopts a VHP by which the HP is arranged to be slower in a data acquiring section corresponding to the heart, indicated with the bi-directional arrow. Further, as another scan condition of the plan A, for example, "DFOV: Matrix Size 512; Reconstruction Mode: Normal Reconstruction" is set.

The right section of FIG. 8A illustrates scan conditions of the plan B. In this situation, as one of the scan conditions of the plan B, a data acquiring condition 55a is set by which an imaging process is performed by using a normal radiation dose in the position corresponding to the region of interest. For example, according to the data acquiring condition 55a, the HP is arranged to be slower in a data acquiring section corresponding to the lesion site 53a. Further, as another scan condition of the plan B, for example, "DFOV: Matrix Size 1024; Reconstruction Mode: High Precision Reconstruction" is set.

In that situation, the setting function 37b sets a data acquiring condition of a plan obtained by integrating together the plan A and the plan B. More specifically, the setting function 37b sets the data acquiring condition illustrated in FIG. 8B. For example, as illustrated in the right section of FIG. 8B, the setting function 37b sets a data acquiring condition 56a in such a manner that the helical pitch is slower in the data acquiring section corresponding to the heart and in the data acquiring section corresponding to the lesion site 53a. Further, the setting function 37b sets a reconstruction condition by which an image is reconstructed in a normal manner in the image taking area of the plan A, whereas a high precision image is reconstructed in the image taking area of the plan B.

Third Modification Example of First Embodiment

Figure 9A:
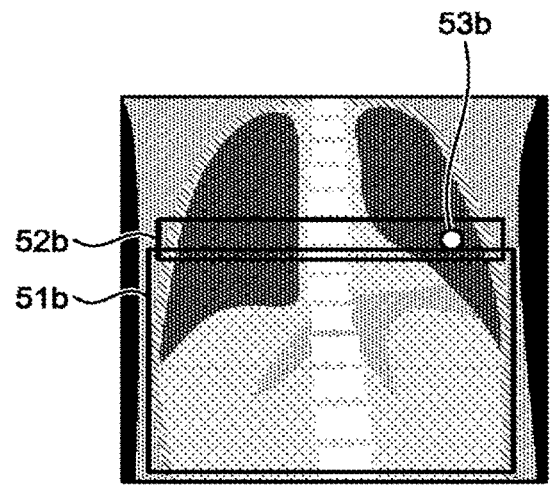
FIG. 9A is a first drawing for explaining a third modification example of the first embodiment.
Figure 9B:
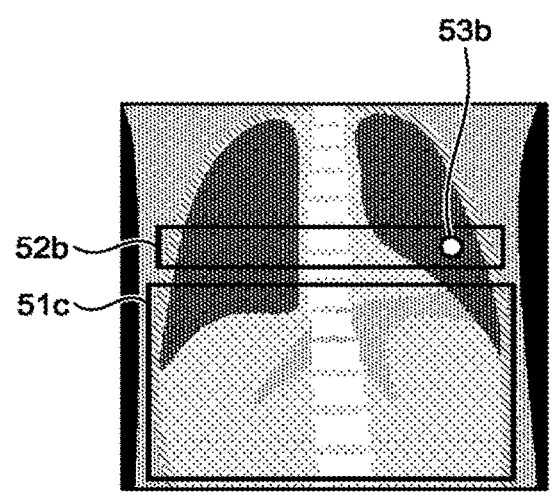
FIG. 9B is a second drawing for explaining the third modification example of the first embodiment.
Figure 9C:
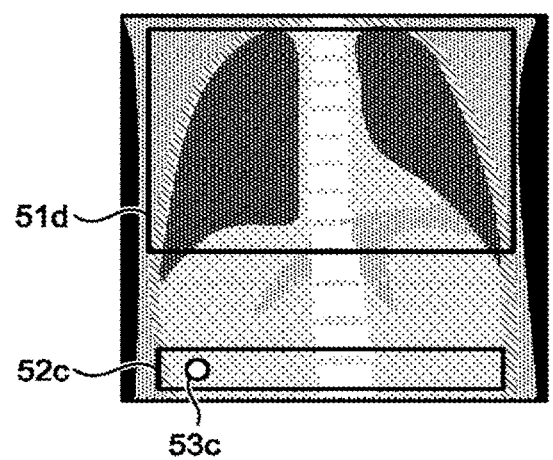
FIG. 9C is a third drawing for explaining the third modification example of the first embodiment.

Further, in the first embodiment above, the example is explained in which the image taking region of the plan A includes the image taking region of the plan B; however, possible embodiments are not limited to this example. FIGS. 9A to 9C are drawings for explaining a third modification example of the first embodiment. For example, as illustrated in FIG. 9A, the embodiment described above is also applicable to a situation where an image taking region 51b of a plan A and an image taking region 52b of a plan B partially overlap each other. As another example, as illustrated in FIG. 9B, the embodiment described above is also applicable to a situation where an image taking region 51c of a plan A and the image taking region 52b of a plan B are positioned adjacent to each other. As yet another example, as illustrated in FIG. 9C, the embodiment described above is also applicable to a situation where an image taking region 51d of a plan A and an image taking region 52c of a plan B are positioned apart from each other to some extent.

Second Embodiment

In the first embodiment described above, the example is explained in which, when the imaging process is performed on the follow-up patient to image the examined site and the region of interest included in the examined site, the data acquiring condition used for imaging the examined site and the data acquiring condition used for imaging the region of interest are put together info one data acquiring condition. In this regard, when a lung cancer CT medical examination is performed on the chest, there may be some situations where a plurality of regions of interest are imaged without imaging the examined site.

Thus, in a second embodiment, an example will be explained in which, when a plurality of regions of interest are imaged without imaging an examined site, the data acquiring conditions of the regions of interest are put together into one data acquiring condition. The overall configuration of an X-ray CT apparatus according to the second embodiment is the same as the exemplary configuration illustrated in FIG. 1, except that some of the operations performed by the setting function 37b are different. Thus, in the following sections, only the setting function 37b will be explained, and detailed explanations of the constituent elements other than the setting function 37b will be omitted.

Figure 10:
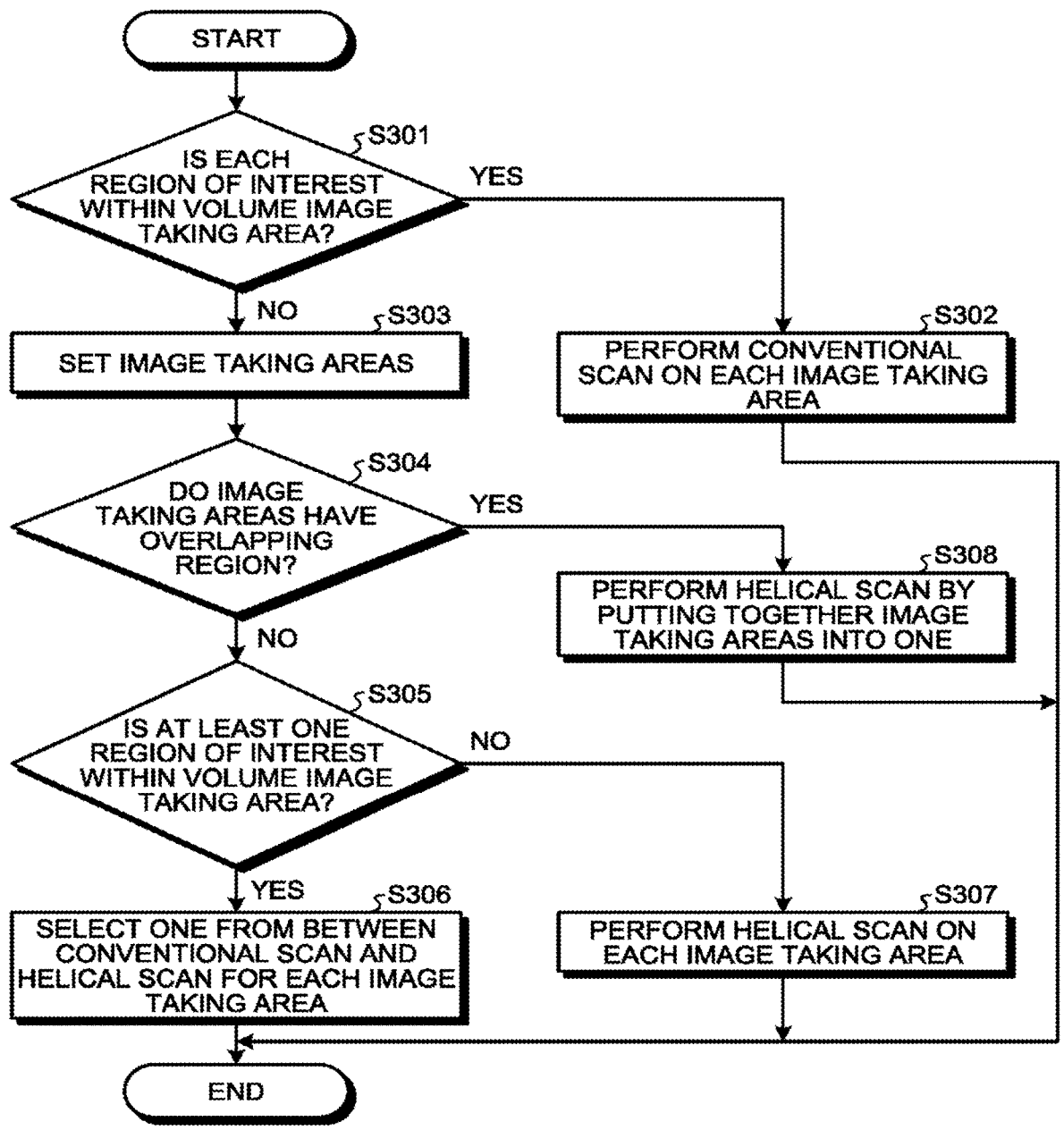
FIG. 10 is a flowchart illustrating a processing procedure performed by a setting function according to a second embodiment.

Further, the processing procedure performed by the X-ray CT apparatus 1 according to the second embodiment is the same as the processing procedure illustrated in FIG. 3, except that the processing procedure at step S103 is different. For example, at step S101, the input circuitry 31 receives the scan conditions of each of the plans. At step S102, the obtaining function 37a obtains the scan conditions of each of the plans. For example, the obtaining function 37a obtains first scan conditions including a data acquiring condition for a first image taking area including a first region of interest and second scan conditions including a data acquiring condition for a second image taking area including a second region of interest. In the following sections, a processing procedure at step S103 will be explained with reference to FIG. 10. FIG. 10 is a flowchart illustrating a processing procedure performed by the setting function 37b according to the second embodiment.

Steps S301 through S308 illustrated in FIG. 10 are steps corresponding to the setting function 37b. As a result of the processing circuitry 37 invoking and executing a predetermined program corresponding to the setting function 37b from the storage circuitry 35, the setting function 37b is realized. With reference to FIG. 10, an example in which two lesion sites are imaged as regions of interest will be explained.

Figure 11A:
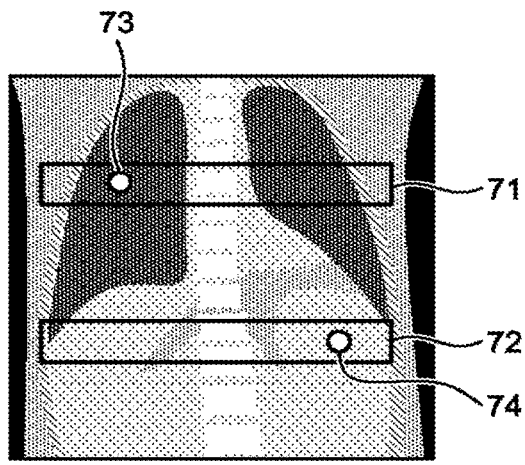
FIG. 11A is a first drawing for explaining a processing operation performed by the setting function according to the second embodiment.
Figure 11B:
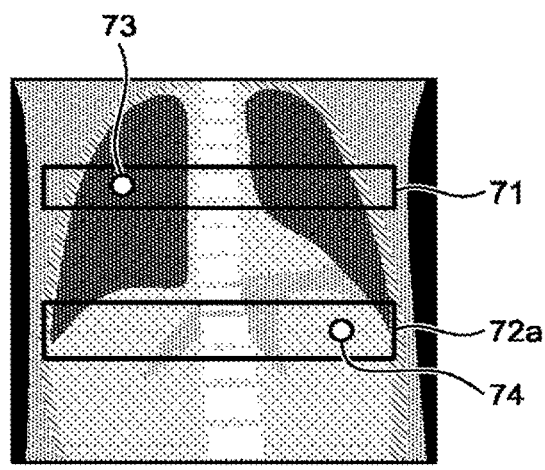
FIG. 11B is a second drawing for explaining the processing operation performed by the setting function according to the second embodiment.
Figure 11C:
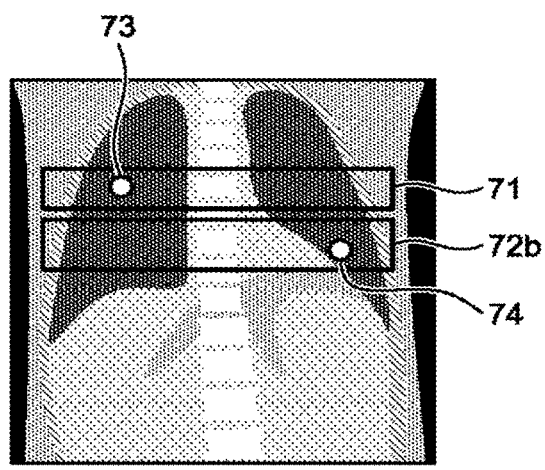
FIG. 11C is a third drawing for explaining the processing operation performed by the setting function according to the second embodiment.

At step S301, the setting function 37b judges whether or not each of the regions of interest is within a volume image taking area. For example, the setting function 37b judges whether or not each of the image taking areas can be fitted in the size of the detector 13. In other words, the setting function 37b judges whether or not it is possible to acquire data from each of the image taking areas including a different one of the regions of interest, by performing one turn of a volume scan. Next, the judging process at step S301 will be explained with reference to FIGS. 11A to 11C. FIGS. 11A to 11C are drawings for explaining a processing operation performed by the setting function 37b according to the second embodiment.

FIGS. 11A to 11C illustrate an example in which a lesion site 73 is imaged as a plan A, whereas a lesion site 74 is imaged as a plan B. In the example in FIG. 11A, an image taking area 71 including the lesion site 73 and another image taking area 72 including the lesion site 74 are set. In the present example, it is assumed that the image taking area 71 and the image taking area 72 are each within a volume image taking area.

In the example illustrated in FIG. 11B, the image taking area 71 including the lesion site 73 and an image taking area 72a including the lesion site 74 are set. In the present example, it is assumed that the image taking area 71 is within the volume image taking area, whereas the image taking area 72a is not within the volume image caking area. Further, in the example illustrated in FIG. 11C, the image taking area 71 including the lesion site 73 and an image taking area 72b including the lesion site 74 are set. In the present example, it is assumed that the image taking area 71 is within the volume image taking area, whereas the image taking area 72b is not within the volume image taking area.

In this situation, when having determined that each of the regions of interest is within the volume image taking area (step S301: Yes), the setting function 37b determines that each of the image taking areas will be imaged by performing conventional scans (step S302). For instance, in the example illustrated in FIG. 11A, the setting function 37b has the image taking area 71 imaged by performing a conventional scan, subsequently moves the couchtop 22, and has the image taking area 72 imaged by performing a conventional scan.

On the contrary, when having determined that at least one of the regions of interest is not within the volume image taking area (step S301: No), the setting function 37b sets image taking areas (step S303). After that, the setting function 37b judges whether or not the image taking areas have one or more overlapping regions (step S304). In other words, the setting function 37b judges whether or not the distance between the first image taking area and the second image taking area is equal to or smaller than a predetermined threshold value. More specifically, in the example illustrated in FIG. 11B, the setting function 37b judges whether or not the distance between the image taking area 71 and the image taking area 72a is equal to or smaller than the predetermined threshold value. Also, in the example illustrated in FIG. 11C, the setting function 37b judges whether or not the distance between the image taking area 71 and the image taking area 72b is equal to or smaller than the predetermined threshold value.

In this situation, when having determined that the image taking areas have no overlapping region (step S304: No), the setting function 37b judges whether or not at least one of the regions of interest is within the volume image taking area (step S305). In one example, in the example illustrated in FIG. 11B, the setting function 37b determines that the distance between the image taking area 71 and the image taking area 72b is not equal to or smaller than the predetermined threshold value and further judges whether or not at least one of the regions of interest is within the volume image taking area. When having determined that at least one of the regions of interest is within the volume image taking area (step S305: Yes), the setting function 37b selects one from between a conventional scan and a helical scan, for each of the image taking areas (step S306). For instance, in the example illustrated in FIG. 11B, when having determined that the image taking area 71 is within the volume image taking area and that the image taking area 72a is not within the volume image taking area, the setting function 37b has the image taking area 71 imaged by performing a conventional scan, subsequently moves the couchtop 22, and has the image taking area 72a imaged by performing a helical scan.

On the contrary, when having determined that none of the regions of interest is within the volume image taking area (step S305: No), the setting function 37b has each of the image taking areas imaged by performing a helical scan (step S307). For example, when having determined that neither of the two image taking areas is within the volume image taking area, the setting function 37b has one of the image taking areas imaged by performing a helical scan, subsequently moves the couchtop 22, and has the other image taking area imaged by performing a helical scan.

In this manner, when both the first image taking area and the second image taking area are each equal to or smaller than the predetermined threshold value, the setting function 37b sets the data acquiring condition of the main scan performed on the first image taking area and the data acquiring condition of the main scan performed on the second image taking area, on the basis of the first scan conditions and the second scan conditions. In another example, when at least one of the first and the second image taking areas is not equal to or smaller than the predetermined threshold value, while the distance between the first image taking area and the second image taking area is not equal to or smaller than the predetermined threshold value, the setting function 37b sets the data acquiring condition of the main scan performed on the first image taking area and the data acquiring condition of the main scan performed on the second image taking area, on the basis of the first scan conditions and the second scan conditions. Further, the setting function 37b sets the data acquiring condition by which the data is acquired by performing one turn of a volume scan on such an image taking area between the first image taking area and the second image taking area that is equal to or smaller than the predetermined threshold value. The setting function 37b also sets the data acquiring condition by which the data is acquired by performing at helical scan on such an image taking area between the first image taking area and the second image taking area that is not equal to or smaller than the predetermined threshold value.

Further, when having determined that the image taking areas has an overlapping region (step S304: Yes), the setting function 37b puts the image taking areas together into one image taking area and performs a helical scan (step S308). For instance, in one example illustrated in FIG. 11C, when having determined that the image taking area 71 and the image taking area 72b have an overlapping region, the setting function 37b images both the image taking area 71 and the image taking area 72b by performing a helical scan, as one image taking plan.

Figure 11D:
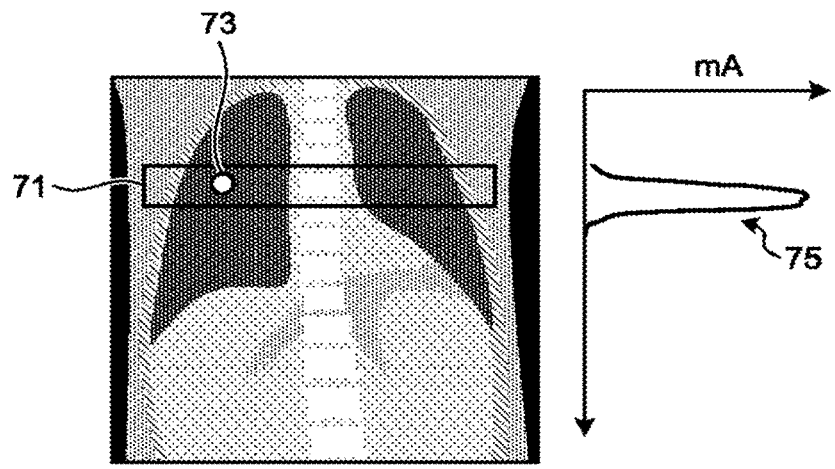
FIG. 11D is a fourth drawing for explaining the processing operation performed by the setting function according to the second embodiment.
Figure 11E:
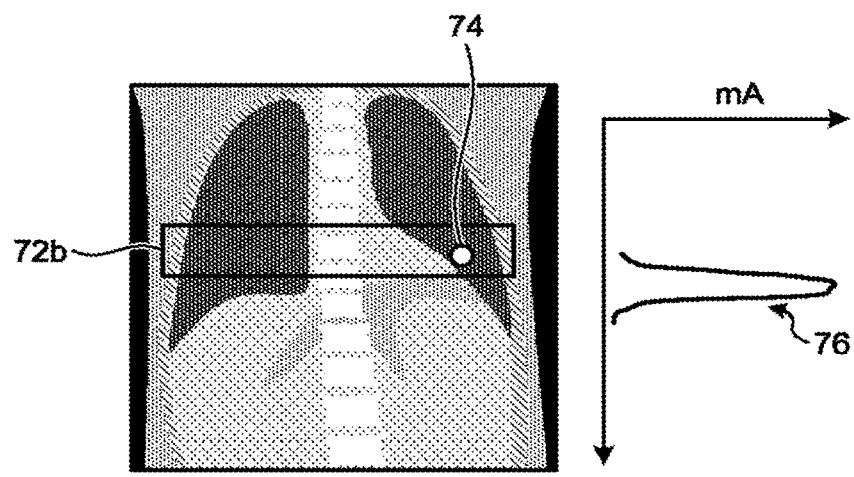
FIG. 11E is a fifth drawing for explaining the processing operation performed by the setting function according to the second embodiment.
Figure 11F:
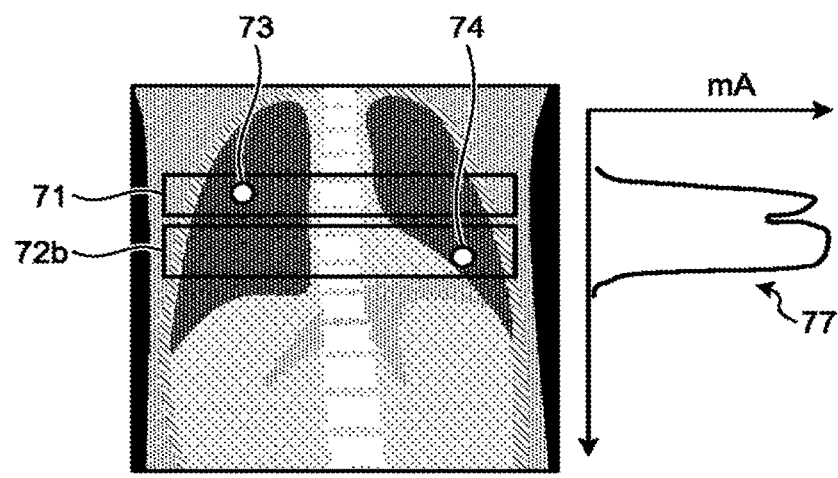
FIG. 11F is a sixth drawing for explaining the processing operation performed by the setting function according to the second embodiment.

Next, the process of putting together the image taking areas into one image taking area at step S308 will be explained with reference to FIGS. 11D to 11F. FIGS. 11D to 11F are drawings for explaining the processing operation performed by the setting function 37b according to the second embodiment.

The left section of FIG. 11D illustrates the image taking area 71 including the lesion site 73, whereas the right section of FIG. 11D illustrates a scan condition of the plan A. As scan conditions, the obtaining function 37a obtains a data acquiring condition 75 illustrated in the right section of FIG. 11D and an image reconstruction condition. The left section of FIG. 11E illustrates the image taking area 72b including the lesion site 74, whereas the right section of FIG. 11E illustrates a scan condition of the plan B. As scan conditions, the obtaining function 37a obtains at data acquiring condition 76 illustrated in the right section of FIG. 11E and an image reconstruction condition.

Subsequently, the setting function 37b obtains position information of a region of interest. For example, the setting function 37b obtains the position information of the region of interest, on the basis of either a position determining image or a CT image related to a medical examination performed on the patient in the past. In one example, as illustrated in the left section of FIG. 11F, the setting function 37b obtains position information of the lesion site 73 and position information of the lesion site 74 that were detected from the CT image related to the medical examination performed on the patient in the past.

After that, she setting function 37b puts together the data acquiring condition 75 of the plan A and the data acquiring condition 76 of the plan B into one data acquiring condition 77. The data acquiring condition 77 illustrated in the right section of FIG. 11F is a data acquiring condition implemented in a helical scan. More specifically, as illustrated in the right section of FIG. 11F, the setting function 37b modulates the X-ray tube current so as to put together the data acquiring condition 75 of the plan A and the data acquiring condition 76 of the plan B, in such a manner that the imaging processes are performed by using a normal radiation dose in the positions of the lesion site 73 and the lesion site 74. In that situation, the X-ray tube current in a position between the position of the lesion site 73 and the position of the lesion site 74 is equal to an X-ray tube current used for performing an imaging process by using an ultra-low radiation dose.

In this situation, when putting together the data acquiring condition 75 of the plan A and the data acquiring condition 76 of the plan B into the one data acquiring condition 77, the setting function 37b may arrange the helical pitch in the region of interest to be slower than the helical pitch in the region other than the region of interest.

In this situation, the reconstructing function 37c reconstructs an image on the basis of the scan conditions of each of the plans. For example, by using data acquired under the set data acquiring condition, the reconstructing function 37c reconstructs images each under the image reconstruction condition included in the first scan conditions and under the image reconstruction condition included in the second scan conditions. More specifically, the reconstructing function 37c reconstructs an image under the image reconstruction condition of the plan A, by using the data acquired under the data acquiring condition 77. Further, the reconstructing function 37c reconstructs another image under the image reconstruction condition of the plan B, by using the data acquired under the data acquiring condition 77. After that, the processing circuitry 37 causes the display 32 to display the reconstructed images of the plans. For example, the processing circuitry 37 causes the display 32 to display the image of the plan A and the image of the plan B. Alternatively, the processing circuitry 37 causes the display 32 to display a combined image obtained by combining together the image of the plan A and the image of the plan B. In another example, the processing circuitry 37 causes the display 32 to display the image of the plan A, the image of the plan B, and a combined image obtained by combining together the image of the plan A and the image of the plan B.

As explained above, for example, when implementing the two plans set independently of each other, the X-ray CT apparatus 1 according to the second embodiment is configured to set the data acquiring condition by which the imaging process is performed as the single plan, on the basis of the acquiring conditions of the two plans. With this arrangement, the operator of the X-ray CT apparatus 1 simply needs to press the imaging start button only once. As a result, the operator of the X-ray CT apparatus 1 is able to perform the medical examination more efficiently.

Further, in the second embodiment, when at least one of the first and the second image taking areas is not equal to or smaller than the predetermined threshold value, while the distance between the first image taking area and the second image taking area is equal to or smaller than the predetermined threshold value, the setting function 37b is configured to set the data acquiring condition of the main scan performed on the first image taking area and the second, image taking area, on the basis of the first scan conditions and the second scan conditions. As a result, according to the second embodiment, it is possible to reduce the number of times the X-rays are radiated onto the extra margin area when the distance between the regions of interest is short. As explained herein, according to the second embodiment, it is possible to reduce the radiation exposure, while making the medical examination more efficient.

Further, in the second embodiment, when it is possible to complete the imaging process within a time period designated by a verbal breathing instruction provided at one time, the imaging process may be performed during the one respiratory time period. In contrast, when the duration for which the patient needs to hold his/her breath is longer than fifteen seconds, for example, the imaging process may be performed in two separate sessions. In either of these situations, the judgment is made on the basis of the imaging time period including the additional moving time.

Other Embodiments

Possible embodiments are not limited to the exemplary embodiments described above.

In the embodiments described above, the example is explained in which the setting function 37b modulates the X-ray tube current; however, possible embodiments are not limited to this example. For instance, the setting function 37b may modulate the X-ray tube voltage.

Further, in any of the embodiments described above, another arrangement is acceptable in which, when the main scan has been performed, the starting position and the ending position of the image taking area of the main scan and the examined site of the main scan are recorded on the basis of the position determining image. In that situation, when the patient undergoes follow-up medical examinations in the future, the setting function 37b is able to automatically set a data acquiring condition after taking a position determining image.

Further, although the embodiments above are explained on the assumption that an example of the region of interest is the lesion site, possible embodiments are not limited to this example. For instance, the region of interest may be a site suspected to be a lesion that is detected from either a position determining image or a CT image related to a medical examination performed in the past.

Further, in the embodiments described above, the example is explained in which the image reconstruction condition includes, for example "Display Field Of View (DFOV): Matric Size 512; Reconstruction Mode: Normal Reconstruction" or "DFOV: Matrix Size 1024; Reconstruction Mode: High Precision Reconstruction". However, possible embodiments are not limited to this example. For instance, the image reconstruction condition may include any of the following: a parameter related to radiation exposure reducing technology to which a reconstruction mathematical function or a successive approximation reconstruction method is applied; a parameter related to an image processing condition corresponding to each site; and a parameter related to an image processing condition used for reducing metal artifacts.

Further, in the embodiments described above, the example is explained in which the relative position between the gantry 10 and the couchtop 22 is changed by controlling the couchtop 22; however, possible embodiments are not limited to this example. For instance, when the gantry 10 is self-propelled, the relative position between the gantry 10 and the couchtop 22 may be changed by controlling the self-propelled movement of the gantry 10.

Figure 12:
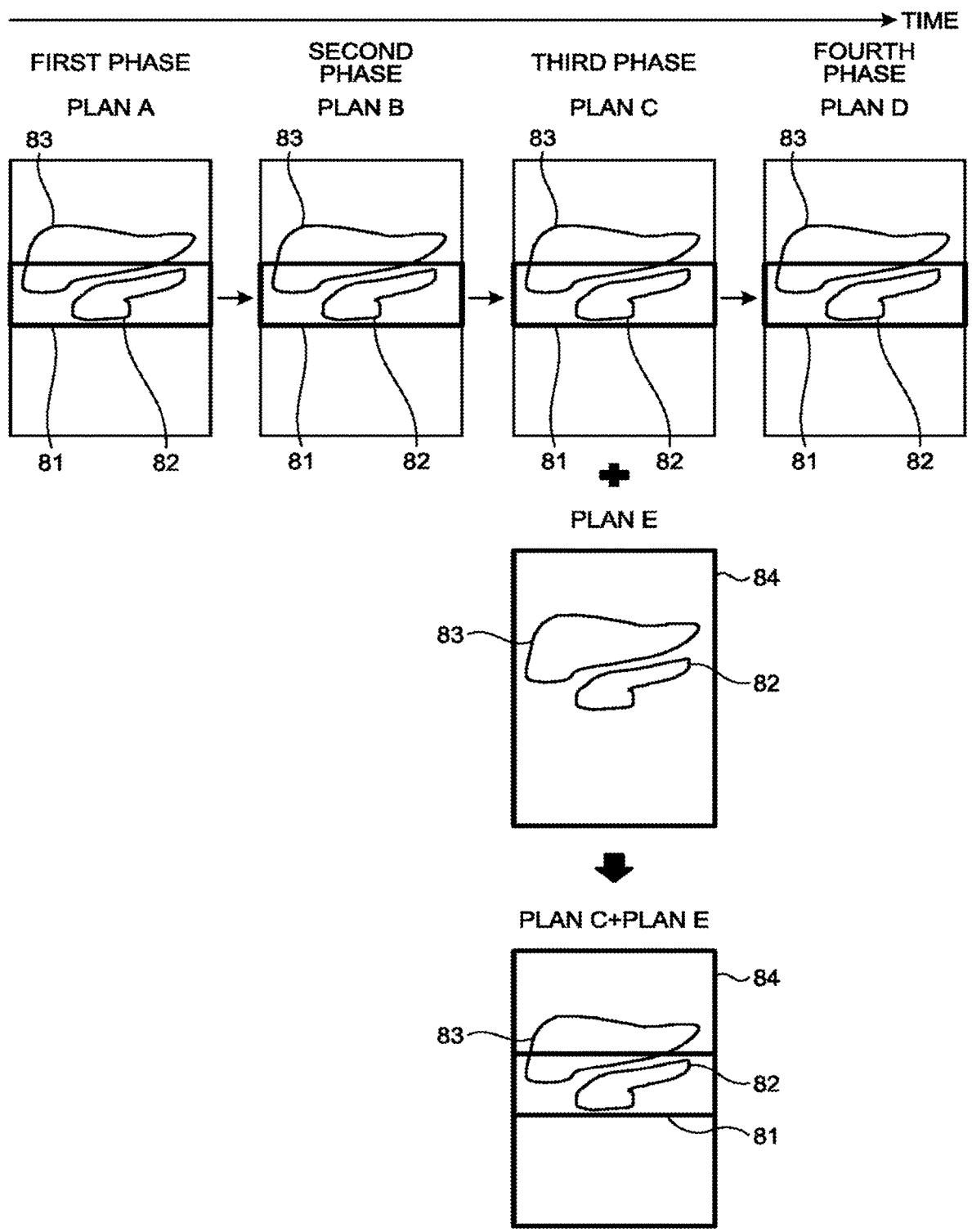
FIG. 12 is a drawing for explaining another embodiment.

Further, in the embodiments described above, the example is explained in which an example of the region of interest is the lesion site; however, possible embodiments are not limited to tin is example. For instance, the region of interest may be an organ included in an examined site. FIG. 12 is a drawing for explaining another embodiment.

With reference to FIG. 12, an example will be explained in which a four-phase imaging process is performed on the pancreas serving as a region of interest. For example, when the four-phase imaging process is performed on the pancreas, an imaging process is performed once in the absence of contrast agents, and subsequently as illustrated in FIG. 12, an imaging process is performed, on the region of interest four times in a plurality of temporal phases, namely first to fourth phases, in accordance with elapsed time periods after administration of a contrast agent. In one example, the imaging process in the first phase is performed when 25 seconds have elapsed since the administration of the contrast agent; the imaging process in the second phase is performed when 40 seconds have elapsed since the administration of the contrast agent; the imaging process in the third phase is performed when 90 seconds have elapsed since the administration of the contrast agent; and the image process in the fourth phase is performed when 3 minutes have elapsed since the administration of the contrast agent. In this manner, during the four-phase imaging process on the pancreas, the imaging process is performed on the region of interest in the plurality of temporal phases in accordance with the elapsed time periods since the administration of the contrast agent.

In the present example, the first phase is a phase in which arteries are rendered. The second phase is a phase in which arteries and veins are rendered. The third phase is a phase in which lymph nodes are rendered after the contrast agent has spread throughout the entire body of the patient. The fourth phase is a phase in which a tumor is dyed in a protracted manner. Further, in that situation, image taking areas and scan conditions are set independently for the imaging process in the first phase, for the imaging process in the second phase, for the imaging process in the third phase, and for the imaging process in the fourth phase. In the present example, mutually the same image taking area 81 is set for the imaging processes of all the temporal phases. The image taking area 81 includes a part of the liver 83 and the entirety of the pancreas 82. Further, mutually the same scan conditions are set for the imaging processes of all the temporal phases. For example, when it is assumed that the X-ray CT apparatus 1 is capable of imaging, in one turn, an area that is 160 mm long in the body axis direction, the entirety of the pancreas 82 serving as the region of interest is within a volume image taking area. Accordingly, for the imaging process in each of the temporal phases, as a scan condition, a data acquiring condition is set by which the image taking area 81 is to be imaged by performing a conventional scan once while arranging the X-ray tube current to be 300 mA. In other words, in the four-phase imaging process performed on the pancreas, the imaging processes in the plurality of temporal phases are performed while using mutually-the-same scan condition. In the following sections, the imaging process in the first phase will be referred to as a plan A, the imaging process in the second phase will be referred to as a plan B, the imaging process in the third phase will be referred to as a plan C, and the imaging process in the fourth phase will be referred to as a plan D, for the sake of convenience in the explanation.

As additional information, when such a four-phase imaging process is performed on the pancreas, for the purpose of closely examining the pancreas serving as the region of interest and checking to see whether or not metastasis to another organ in the abdomen serving as the examined site has occurred, a region that is larger in area and that includes the pancreas is also imaged during the imaging process of one of the temporal phases. In other words, the imaging process on the examined site is performed in a predetermined one of the plurality of temporal phases. The imaging process on the examined site may be performed, for example, when 90 seconds have elapsed since the administration of the contrast agent. In that situation, for example, an image taking area 84 that is larger in area and includes the entire abdomen is set as the examined site. In that situation, alternatively, an image taking area that is larger in area and includes the region from above the neck to the pelvis of the patient P may be set as the examined site. Further, in that situation, for example, as a scan condition, a data acquiring condition is set by which the image taking area 84 is to be imaged by performing a helical scan while the X-ray tube current is arranged to be 200 mA. In the following sections, the imaging process performed on the examined site in the predetermined temporal phase will be referred to as a plan E, for the sake of convenience in the explanation.

Further, after image taking plans are set for the plan A, the plan B, the plan C, the plan E, and the plan D in the stated order, the imaging processes according to the plans are performed. In this situation, according to the conventional technique, the imaging process in the third phase according to the plan C and the imaging process on the larger region according to the plan E would be performed independently of each other. Accordingly, the radiation exposure would be duplicate on the part of the liver 83 and the entirety of the pancreas 82 that are included in both the image taking area 81 of the plan C and the image taking area 84 of the plan E.

In contrast, according to the present other embodiment, a data acquiring condition is set by which, during the imaging process in the third phase, the imaging process of the plan C and the imaging process of the plan E are performed together. For example, when performing the imaging processes on the region of interest in the plurality of temporal phases in accordance with the elapsed time periods since the administration of the contrast agent as well as the imaging process on the examined site in a predetermined one of the plurality of temporal phases, the setting function 37b sets the data acquiring condition of the main scan performed in the predetermined temporal phase in the following manner: The setting function 37b sets the data acquiring condition of the main scan to be performed on the examined site of the patient P including the pancreas 82 serving as the region of interest, on the basis of scan conditions including the data acquiring condition for the imaging process in the third phase in which the image taking area 81 is set and scan conditions including the data acquiring condition for the imaging process performed on the larger region in which fine image taking area 84 is set. In other words, the setting function 37b sets the data acquiring condition of the main scan for the imaging process performed in the predetermined temporal phase, on the basis of first scan conditions including the data acquiring condition for the imaging process in the predetermined temporal phase and second scan conditions including the data acquiring condition for the imaging processes in the plurality of temporal phases.

More specifically, for such an area of the image taking area 84 that does not overlap with the image taking area 31, the setting function 37b sets a scan condition by which the area is imaged by performing a helical scan while the X-ray tube current is arranged to be 200 mA. For such an area of the image taking area 84 that overlaps with the image taking area 81, the setting function 37b sets a data acquiring condition as a scan condition by which the area is imaged by performing a helical scan while the X-ray tube current is arranged to be 300 mA and the helical pitch is arranged to be slower. In this manner, the setting function 37b sets the date acquiring condition of the plan obtained by integrating together the plan C and the plan E.

In this situation, when setting the data acquiring condition of the plan obtained by integrating together the plan C and the plan E, the setting function 37b may receive a designation of an order of priority levels between the time at which the imaging process of the plan C is started and the time at which the imaging process of the plan E is started. In other words, the setting function 37b sets the data acquiring condition of the main scan by which the starting time of the imaging process according to the scan condition of the plan C and the starting time of the imaging process according to the scan condition of the plan E are designated with the order of priority levels. For example, when setting the data acquiring condition of the plan obtained by integrating together the plan C by which the imaging process is started when 90 seconds have elapsed since the administration of the contrast agent and the plan E by which the imaging process is started when 100 second have elapsed since the administration of the contrast agent, the setting function 37b may receive a designation indicating that a higher priority should be given to one selected from the starting time of the imaging process of the plan C and the starting time of the imaging process of the plan E. In one example, when having received a designation indicating that a higher priority is given to the starting time of the imaging process of the plan C, the setting function 37b sets the starting time of the imaging process of the plan E, by calculating backward so that the imaging process of the plan C is started when 90 seconds have elapsed since the administration of the contrast agent. In the present example, let us assume that it takes three seconds to start the imaging process of the plan C after the imaging process of the plan E is started. In that situation, the setting function 37b sets the times in such a manner that the imaging process of the plan C is started when 90 seconds have elapsed since the administration of the contrast agent and that the imaging process of the plan E is started when 87 seconds have elapsed since the administration of the contrast agent. On the contrary, when the setting function 37b receives a designation indicating that a higher priority is given to the starting time of the imaging process of the plan E, the imaging process of the plan E is started when 100 seconds have elapsed since the administration of the contrast agent. In that situation, the setting function 37b sets the time in such a manner that the imaging process of the plan E is started when 103 seconds have elapsed since the administration of the contrast agent. Alternatively, the setting function 37b does not necessarily have to receive a designation of the order of priority levels with respect to the starting times of the imaging processes of the plan C and the plan E. In that situation, the setting function 37b sets a time in the middle of the starting time of the imaging process of the plan C and the starting time of the imaging process of the plan E, as a time at which the imaging process is started. For example, the setting function 37b sets the time so that one of the imaging processes is started at 95 seconds. For example, the setting function 37b may set the time so that the imaging process of the plan E is started when 95 seconds have elapsed since the administration of the contrast agent or may set the time so that the imaging process of the plan C is started when 35 seconds have elapsed since the administration of the contrast agent.

After that, when the four-phase imaging process on the pancreas has been finished, the reconstructing function 37c reconstructs an image under the image reconstruction condition included in the scan conditions of the plan E by using the data acquired under the data acquiring condition set for the predetermined temporal phase. Also, the reconstructing function 37c reconstructs an image under the image reconstruction condition included in the scan conditions of the plans A to D by using the pieces of data acquired in the temporal phases.

More specifically, the reconstructing function 37c reconstructs an image (the image in the first phase) of the image taking area 81 under the image reconstruction condition included in the scan conditions of the plan A, by using the data acquired in the first phase. The reconstructing function 37c reconstructs an image (the image in the second phase) of the image taking area 81 under the image reconstruction condition included in the scan conditions of the plan B, by using the data acquired in the second phase. The reconstructing function 37c further reconstructs an image (the image in the third phase) of the image taking area 81 under the image reconstruction condition included in the scan conditions of the plan C, by using the data acquired in the third phase. The reconstructing function 37c also reconstructs an image (the image in the fourth phase) of the image taking area 81 under the image reconstruction condition included in the scan conditions of the plan D, by using the data acquired in the fourth phase. After that, the reconstructing function 37c reconstructs an image (the image of the examined site) of the image taking area 84 under the image reconstruction condition included in the scan conditions of the plan E by using the data acquired in the third phase. In this situation, the reconstructing function 37c identifies the image talking area 81 of the conventional scan from the data acquired in one third phase and reconstructs the image in the third phase under the image reconstruction condition included in the scan conditions of the plan C.

After that, the processing circuitry 37 exercises control so that the display 32 displays the reconstructed pieces of image data. In this situation, for example, the processing circuitry 37 causes the display 32 to display the image in the first phase, the image in the second phase, the image in the third phase, and the image in the fourth phase, as well as to display the image of the examined site. Alternatively, for example, when arranging the image in the first phase, the image in the second phase, the image in the third phase, and the image in the fourth phase to be displayed, the processing circuitry 37 may cause the display 32 to display the slice positions being displayed so as to be in synchronization with one another among the images. In other words, the processing circuitry 37 may cause the display 32 to display the slice position of the image in the third phase, the slice position of the image in the first phase, the slice position of the image in the second phase, and the slice position of the image in the fourth phase, so as to be in synchronization with one another. With these arrangements, when interpreting the images corresponding to the different temporal phases, a person who interprets the images is able to easily make a comparison among the images corresponding to the different temporal phases.

In the embodiment above, the example is explained in which the four-phase imaging process is performed on the pancreas serving as the region of interest; however, possible embodiments are not limited to this example. For instance, the region of interest may be a kidney or the liver. Further, a plurality of regions of interest may be set. For example, the liver and the pancreas may be set as regions of interest. In that situation, the setting function 37b sets a data acquiring condition of the main scan including the plurality of regions of interest, on the basis of scan conditions of the entire abdomen and scan conditions of each of the regions of interest.

Further, in the embodiments above, the example is explained in which, when performing the reconstruction process, the reconstructing function 37c generates the images having the mutually-different resolutions from the projection data based on the detection data detected in the high precision mode. For example, the reconstructing function 37c reconstructs the image having the lower resolution by bundling the high precision projection data or generates the image having the lower resolution by reconstructing the high precision image and subsequently bundling the reconstructed image. However, possible embodiments are not limited to these examples. For instance, the image having the lower resolution may be generated as a result of either the detector 13 or the data acquiring circuitry 14 bundling detection data detected by the detector 13 in the high precision mode.

In the following sections, an example will be explained in which a third plan is set by integrating together a plan A for an examined site of the patient P and a plan B for a region of interest included in the examined site. In the plan A, for example, a data acquiring condition is set by which the entire chest is imaged by using an ultra-low radiation dose. Further, in the plan B, for example, a data acquiring condition is set by which an image is reconstructed with a higher precision than the level of precision in the plan A, by arranging the helical pitch in the region of interest to be at a lower speed than the helical pitch in the region other than the region of interest. Further, as the third plan, as explained in the first embodiment, for example, a plan obtained by integrating together the plan A and the plan B is set.

After that, according to the third plan, the detector 13 detects pieces of high precision detection data from the detecting elements arranged in the 160 rows corresponding to the 1792 channels. Further, the detector 13 outputs the pieces of high precision detection data to the data acquiring circuitry 14. In this situation, in the data acquiring section of the plan A, the data acquiring circuitry 14 generates projection data having a lower resolution by bundling the high precision detection data. For example, the data acquiring circuitry 14 generates the projection data having a lower resolution by putting together every four detecting elements as one unit and further adding together pieces of high precision projection data corresponding to the four detecting elements combined in one unit. After that, the data acquiring circuitry 14 outputs the generated projection data to the pre-processing circuitry 34.

Further, in the data acquiring section of the plan B, the data acquiring circuitry 14 generates projection data having a high resolution without bundling high precision detection data and outputs the high precision projection data to the pre-processing circuitry 34. In this manner, according to the third plan, the data acquiring circuitry 14 acquires a first piece of defection data corresponding to a first resolution that is a high precision resolution and a second piece of detection data corresponding to a second resolution that is lower than the first resolution, by bundling the data corresponding to the first resolution.

After that, the reconstructing function 37c reconstructs an image having the first resolution from the first piece of detection data and reconstructs an image having the second resolution from the second piece of detection data. For example, the reconstructing function 37c reconstructs an image corresponding to the image taking area of the plan B, from the projection data having a higher resolution and being acquired according to the third plan. Further, the reconstructing function 37c reconstructs an image corresponding to the image taking area of the plan A, from the projection data having the lower resolution and being acquired according to the third plan. In this situation, the image taking area of the plan A includes the image taking area of the plan B. Accordingly, in such an area of the image taking area of the plan A that overlaps with the plan B, the image is reconstructed from the projection data having the higher resolution. For this reason, when reconstructing the image corresponding to the image taking area of the plan A, the reconstructing function 37c reconstructs the image corresponding to the image taking area of the plan A after bundling the projection data in the overlapping area between the plan A and the plan B.

The constituent elements of the apparatuses and the devices illustrated in the drawings in the embodiments above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally cue physically distribute or integrate all or a part of the apparatuses and the devices in any arbitrary units, depending on various loads and the status of use. Further, all or an arbitrary part of the processing functions performed by the apparatuses and the devices may be realized by a CPU and a computer program analyzed and executed by the CPU or may be realized as hardware using wired logic.

Further, it is possible to realize the controlling method explained in the embodiments above, by causing a computer such as a personal computer or a workstation to execute a control computer program (hereinafter, "control program"; prepared in advance. It is possible to distribute the control program via a network such as the Internet. Further, the control program may be executed as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

According to at least one aspect of the embodiments described above, it is possible to reduce the radiation exposure, while making the medical examinations more efficient.

While certain embodiments have been described, these embodiments have been presented, by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a detector having a first resolution;
   setting circuitry configured to set, based on a first plan and a second plan, a third data acquiring condition to acquire data of a first image taking area and a second image taking area of a patient by performing a single scan, the first plan including a first data acquiring condition and a first image reconstruction condition for the first image taking area, the second plan including a second data acquiring condition and a second image reconstruction condition for the second image taking area;
   acquiring circuitry configured to acquire, according to the third data acquiring condition, data corresponding to the first resolution; and
   reconstructing circuitry configured to reconstruct a first image according to the first image reconstruction condition and reconstruct a second image according to the second image reconstruction condition,
   wherein the reconstructing circuitry reconstructs the first and the second images from the data corresponding to the first resolution, one of the first and the second images having the first resolution, the other of the first and the second images having a second resolution lower than the first resolution.

2. The X-ray CT apparatus according to claim 1, wherein, based on the first plan for an imaging target site of the patient and the second plan for a region of interest included in the imaging target site, the setting circuitry sets the third data acquiring condition for the imaging target site of the patient including the region of interest.

3. The X-ray CT apparatus according to claim 2, wherein the setting circuitry sets the third data acquiring condition by which one selected from between an X-ray tube current or an X-ray tube voltage in the region of interest is modulated in comparison to that in a region other than the region of interest.

4. The X-ray CT apparatus according to claim 2, wherein the setting circuitry sets the third data acquiring condition by which a helical pitch in the region of interest is arranged to be at a lower speed than a helical pitch in a region other than the region of interest.

5. The X-ray CT apparatus according to claim 2, wherein the setting circuitry sets the third data acquiring condition by obtaining position information of the region of interest on a basis of one selected from between a position determining image and a CT image related to a past medical examination performed on the patient.

6. The X-ray CT apparatus according to claim 2, wherein
   when a plurality of regions of interest are present, the setting circuitry sets the third data acquiring condition including the plurality of regions of interest, on the basis of the first plan and the second plan corresponding to each of the regions of interest, and
   the reconstructing circuitry reconstructs the first image according to the first image reconstruction condition included in the first plan and the second image according to the second image reconstruction condition included in the second plan corresponding to each of the regions of interest.

7. The X-ray CT apparatus according to claim 2, wherein
   when first imaging processes are to be performed on the region of interest in a plurality of temporal phases in accordance with elapsed time periods since an administration of a contrast agent and an second imaging process is to be performed on the imaging target site, corresponding to the region of interest, in a predetermined one of the plurality of temporal phases, the setting circuitry sets the third data acquiring condition for the imaging process for the predetermined one of the temporal phases, on the basis of the first plan for the first imaging processes in the plurality of temporal phases and the second plan for the second imaging process, and
   the reconstructing circuitry reconstructs the first image based on the first image reconstruction condition included in the first plan and reconstructs the second image under the second image reconstruction condition included in the second plan by using pieces of data acquired in the plurality of temporal phases.

8. The X-ray CT apparatus according to claim 7, wherein the setting circuitry sets the third data acquiring condition designating an order of priority levels among a time at which the imaging process according to the first plan is started and times at which the imaging processes according to the second plan are started.

9. The X-ray CT apparatus according to claim 7, wherein a predetermined display displays a slice position of the image of the region of interest in the predetermined one of the temporal phases reconstructed from the data acquired according to the third data acquiring condition by using the image reconstruction condition included in the second plan, in synchronization with a slice position of the image of the region of interest in the temporal phases other than the predetermined one of the temporal phases reconstructed from data acquired according to the second plan by using the image reconstruction condition included in the second plan.

10. The X-ray CT apparatus according to claim 2, wherein the region of interest is a region including a lesion site within a position determining image of the patient.

11. The X-ray CT apparatus according to claim 1, wherein, from the data corresponding to the first resolution, the reconstructing circuitry reconstructs the first and the second image of which the resolutions are each equal to the first resolution and further performs an image processing process so that the resolution of one of the first and the second images becomes equal to the second resolution.

12. The X-ray CT apparatus according to claim 1, wherein, the reconstructing circuitry reconstructs the one of the first and the second images having the first resolution from the data corresponding to the first resolution and reconstructs the other of the first and the second images having the second resolution from data obtained by bundling the data corresponding to the first resolution so as to have the second resolution.

13. An X-ray CT apparatus comprising:
a detector having a first resolution;
setting circuitry configured to set, based on a first plan and a second plan, a third data acquiring condition to acquire data of a first image taking area and a second image taking area of a patient by performing a single scan, the first plan including a first data acquiring condition and a first image reconstruction condition for the first image taking area, the second plan including a second data acquiring condition and a second image reconstruction condition for the second image taking area;
acquiring circuitry configured to acquire, according to a third data acquiring condition, first data corresponding to the first resolution and acquire second data corresponding to a second resolution lower than the first resolution by bundling the first data corresponding to the first resolution; and
reconstructing circuitry configured to reconstruct a first image according to the first image reconstruction condition and reconstruct a second image according to the second image reconstruction condition by using data acquired according to the third data acquiring condition,
wherein the reconstructing circuitry reconstructs the first image from the first data corresponding to the first resolution and reconstructs the second image from the second data corresponding to the second resolution, one of the first and the second images having the first resolution, the other of the first and the second images having the second resolution.

14. An X-ray CT apparatus comprising:
obtaining circuitry configured to obtain a first plan for a first image taking area including a first region of interest and a second plan for a second image taking area including a second region of interest;
setting circuitry configured to set, according to sizes of the first and the second image taking areas and a distance therebetween, a third plan for the first and the second image taking areas on a basis of the first plan and the second plan; and
reconstructing circuitry configured to reconstruct an image under an image reconstruction condition included in the first plan and an image under an image reconstruction condition included in the second plan, by using data acquired according to the set third plan, wherein,
when at least one of the sizes of the first and the second image taking areas is not equal to or smaller than a first threshold value, while the distance therebetween is equal to or smaller than a second threshold value, the setting circuitry sets a data acquiring condition included in the third plan to acquire data of an area including both the first and the second image taking areas, and
when both the first and the second image taking areas are each equal to or smaller than the first threshold value or when at least one of the first and the second image taking areas is not equal to or smaller than the first threshold value, while the distance therebetween is not equal to or smaller than the second threshold value, the setting circuitry sets a data acquiring condition included in the third plan to acquire data of the first image taking area and a data acquiring condition included in the third plan acquire data of the second image taking area, on a basis of the first plan and the second plan.

15. The X-ray CT apparatus according to claim 14, wherein the setting circuitry sets a data acquiring condition by which data is acquired by performing one turn of a volume scan on one of the first and the second image taking areas of which the size is equal to or smaller than the first threshold value and sets a data acquiring condition by which data is acquired by performing a helical scan on one of the first and the second image taking area that is not equal to or smaller than the first threshold value.

16. An X-ray CT apparatus comprising:
input circuitry configured to set a first area of an object to be examined and a second area overlapped with the first area,
obtaining circuitry configured to obtain a first imaging condition for imaging the first area, and a second imaging condition for imaging the second area of the object;
setting circuitry configured to integrate the first and the second imaging conditions into a third imaging condition for imaging a third area covering the first and the second areas, to avoid duplicate imaging of the overlapped area, wherein in the third imaging condition the second area is imaged based on the second imaging condition;
acquisition circuitry configured to acquire, based on the third imaging condition, a set of projection data from the third area of the object; and reconstructing circuitry configured to reconstruct an image from the set of projection data, wherein the reconstructed image visualizes the third area.

17. The X-ray CT apparatus of claim 16, wherein
the obtaining circuitry is configured to obtain the second imaging condition for imaging the second area included the first area;
the setting circuitry is configured to set the third imaging condition for imaging the third area which is the first area including the second area.

18. The X-ray CT apparatus of claim 16, further comprising:
- display controlling circuitry configured to cause a display to display the third imaging condition; and
- receiving circuitry configured to receive user inputs for modifying the third imaging condition,
- wherein the acquisition circuitry is configured to acquire a set of projection data based on the modified third imaging condition.

19. The X-ray CT apparatus of claim 16, wherein
- the obtaining circuitry is configured to obtain the second imaging condition for imaging the second area partially overlapped with the first area;
- the setting circuitry is configured to set the third imaging condition for imaging the third area which includes the first area and a part of the second area which is not overlapped with the first area.

* * * * *